United States Patent [19]
Levengood et al.

[11] Patent Number: 6,023,880
[45] Date of Patent: Feb. 15, 2000

[54] METHOD AND APPARATUS FOR ENHANCING GROWTH CHARACTERISTICS OF SEEDS USING ION-ELECTRON AVALANCHES

[76] Inventors: William C. Levengood, 4853 Wolf Lake Rd. (P.O. Box 388), Grass Lake, Mich. 49240; John A. Burke, 20 Cyrus Pt. Rd., Bayville, N.Y. 11709

[21] Appl. No.: 08/939,513

[22] Filed: Sep. 29, 1997

Related U.S. Application Data

[62] Division of application No. 08/715,618, Sep. 18, 1996, Pat. No. 5,740,627.

[51] Int. Cl.[7] ...................................................... A01C 1/00
[52] U.S. Cl. ................................................................. 47/1.3
[58] Field of Search .................. 47/1.3, 58.1; 324/117 R

[56] References Cited

U.S. PATENT DOCUMENTS

| | | | |
|---|---|---|---|
| 2,802,182 | 8/1957 | Godshalk et al. | 324/445 |
| 3,546,580 | 12/1970 | Williams | 324/258 |
| 3,652,935 | 3/1972 | Shaw | 324/117 R X |
| 4,100,488 | 7/1978 | Quietzch et al. | 324/117 R X |

Primary Examiner—Michael J. Carone
Assistant Examiner—Jeffrey L. Gellner
Attorney, Agent, or Firm—Ian C. McLeod

[57] ABSTRACT

A method and apparatus for treating seeds with self-organized avalanches of electrons between electrodes (11, 12) as a cathode and an anode with seeds (13) between the anode and cathode or on the anode. Apparatus circuit (200) in a box (20) provides simultaneous DC and AC between the electrodes which creates the avalanche of electrons which project into the seeds. The seeds must be stored before planting. The seeds so treated have enhanced growth characteristics.

6 Claims, 19 Drawing Sheets

METHOD AND APPARATUS FOR ENHANCING GROWTH CHARACTERISTICS OF SEEDS USING ION-ELECTRON AVALANCHES

This is a divisional of application(s) Ser. No. 08/715,618 filed on Sep. 18. 1996, now U.S. Pat. No. 5,740,627.

BACKGROUND OF THE INVENTION (1) Field of the Invention

The present invention relates to a method and apparatus for treating seeds, thereby reproducibly enhancing rate and uniformity of seed germination, early growth, root growth, maturity, and yield in food crops and other plants. These results are achieved by exposing seeds or growing plants to uniform, spontaneously-organized pulses of ion-electron avalanches. One important aspect is allowing a period of several weeks storage before planting thereby allowing internal, biochemical changes to take place at the cellular level within the seed. The present invention also relates to a quality-control method and apparatus for selecting optimal treatment parameters with the avalanches of ions and electrons for each variety of seed.

(2) Description of Related Art

Almost since the discovery of the commercial use of electricity, experimenters have tried to electrically influence plant growth. Various prior art experimenters have claimed positive results from exposing growing plants to electrical stimulation in situ. A wiring network over a field of growing crops is not cost-effective or practical on a commercial scale, and such techniques have not been adopted by farmers.

Some prior art experimenters have attempted to avoid the prohibitive cost of wiring a field by applying electromagnetic treatments to seeds before planting. Despite reports of increased growth and, in some cases, increased yield, these results have proven difficult to repeat and have not achieved commercial use. Parry (U.S. Pat. No. 2,308,204 (1943)) describes the use of an oscillating DC voltage to treat seeds to increase germination of the seeds. There is no indication of improved plants. Jonas (U.S. Pat. No. 2,712,713 (1955)) and others exposed seeds to high frequency oscillating fields between 30 MHz and microwave range, claiming faster and more uniform germination. Jonas stated that the work of others along similar lines have been impossible to repeat and confirm. The patent describes only increased germination of the seeds. Amburn (U.S. Pat. Nos. 3,675,367 (1972) and 3,765,125 (1975)) exposed seeds to magnetic fields, claiming increased germination rate as an effect. Because of unreliability and non-reproducibility, none of these methods have achieved widespread commercial acceptance.

Levengood (U.S. Pat. No. 3,822,505 (1974)) describes an apparatus for genetically altering plant cells using combined electrical and magnetic fields. The electrical field is static. There was alteration in the growth of seeds, but the method was not repetitively effective from batch to batch of seeds. Another patent to Levengood (U.S. Pat. No. 3,852,914 (1974)) describes a method for testing seeds for viability, by measuring pregermination tissue conductivity.

Schiller et al (U.S. Pat. No. 4,633,611 (1987)) describe treating seeds to disinfect them with low energy electrons using an electron gun. The radiation dosages are quite high and the acceleration voltages are between 25 and 75 kV. The use of high energy ionizing radiation can cause damage to chromosomes and resultant genetic change which poses complications for use in open fields. There is no indication that the growth of the plant is enhanced on a reproducible basis. Yoshida (U.S. Pat. No. 4,758,318 (1988)) describes using a pulsating direct current to prevent mold. The voltages were 300 to 20,000 V DC which were pulsed. This method is not practical on a large scale and the results were variable. Liboff et al (U.S. Pat. No. 5,077,934 (1992)) describe the use of magnetic fields with plants in the soil. This method is not practical.

Levengood (U.S. Pat. No. 5,288,626 (1994)) describes genetically transferring DNA between plants using a constant DC voltage. This is also described in Bioelectrochemistry and Bioenergetics (1991). These are techniques for producing genetically altered plants.

Other patents of general interest are Saruwatari (U.S. Pat. No. 4,188,751 (1980)) relating to magnetic treatment; Weinberqer (U.S. Pat. No. 3,703,051 (1972)) relating to ultrasound; U.S. Pat. No. 3,940,885 (1976) relating to microwaves.

One system which used an A.C. ripple in a D.C. current to produce pulses is Tellefson (U.S. Pat. No. 5,117,579 (1992)). Pulses of ions were produced from wire brush emitters to flood growing plants in a field. The method is not used with seeds.

There is clearly a need for a reproducible and reliable method for treating seeds to enhance their growth characteristics. The prior art methods have not met this need since no such method is used commercially.

OBJECTS

It is therefore an object of the present invention to provide an improved, reproducible method and apparatus for enhancing the growth characteristics of seeds. It is further an object of the present invention to provide such a method which is simple, reliable and economical to perform. Further still it is an object of the present invention to provide a method and apparatus for detecting whether or not the treated seeds have been effectively improved in their growth characteristics by the method and apparatus for enhancing growth characteristics Further still, it is an object of the present invention to provide a method and apparatus which allows monitoring during treatment of the effectiveness of the apparatus for performing the treatment. These and other objects will become increasingly apparent by reference to the following specification and the drawings.

BRIEF DESCRIPTION OF DRAWINGS

FIG. 2A shows tomato seeds tested 35 days after exposure. FIG. 2B shows pepper seeds tested 35 days after exposure. FIG. 2C shows carrot seeds tested 36 days after exposure. As can be seen, similar curve shapes appear in the 5-minute exposure data. In every case the maximum peak is at the 5-kV level, with a secondary peak at 20-KV.

FIG. 4 shows redox ratios of MIR-treated carrots to be lower than that of untreated controls, when measured after the plants develop to the mature autotrophic phase. The redox potential is determined from exudate from the seeds.

Figure 5:
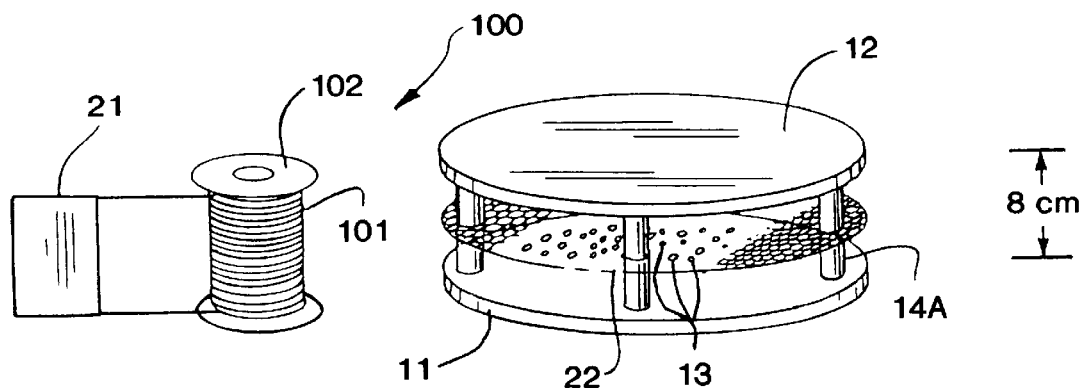
FIG. 5 is a schematic view of an apparatus 100 with a probe coil 101 for examining the induced-energy wave form from the ion-electron avalanche pulses produced by the apparatus of FIG. 1A. The coil 101 had 80,000 turns of #40 copper wire and was approximately 8 cm in diameter and 10 cm long on core 102.
Figure 6:
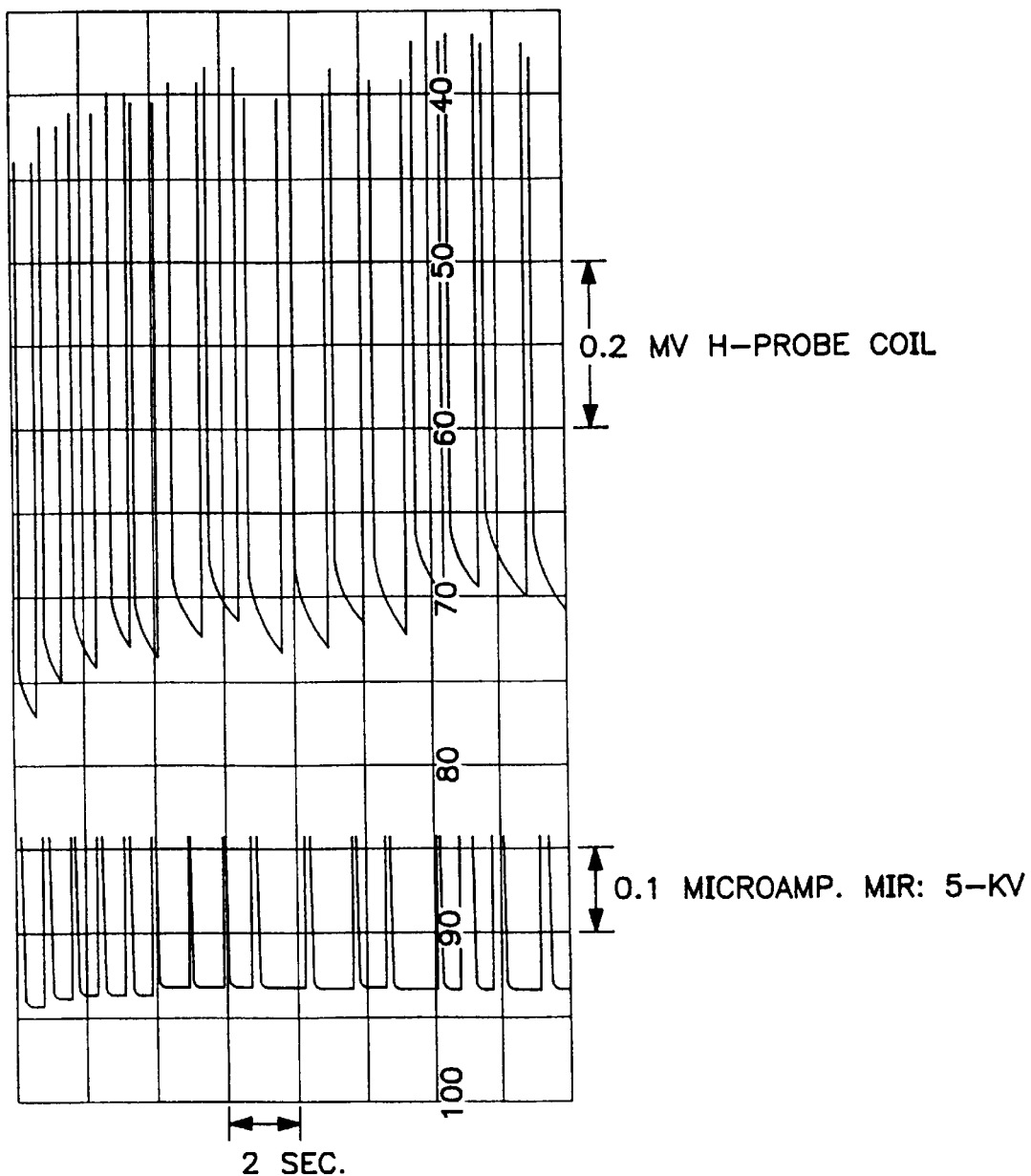

The upper part of FIG. 6 is a graph showing the induced magnetic field in the coil 101 of FIG. 5 produced by the electron avalanches shown in the lower portion of FIG. 6. This gives a direct reading of the current between the electrodes 11 and 12 of FIG. 1A at an applied potential of 5 kV.

Figure 7:
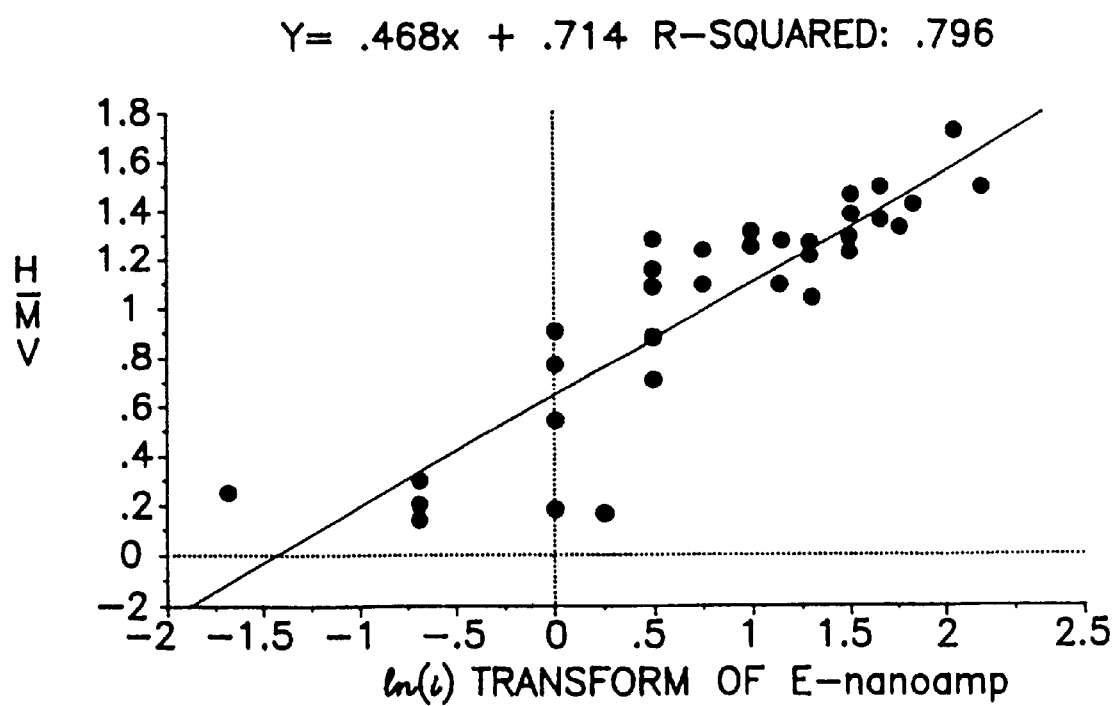

FIG. 7 is a graph showing an exponential correlation between the electron pulsed current between electrodes 11 and 12 and the magnetic field potential induced in the coil 101.

Figure 8A:
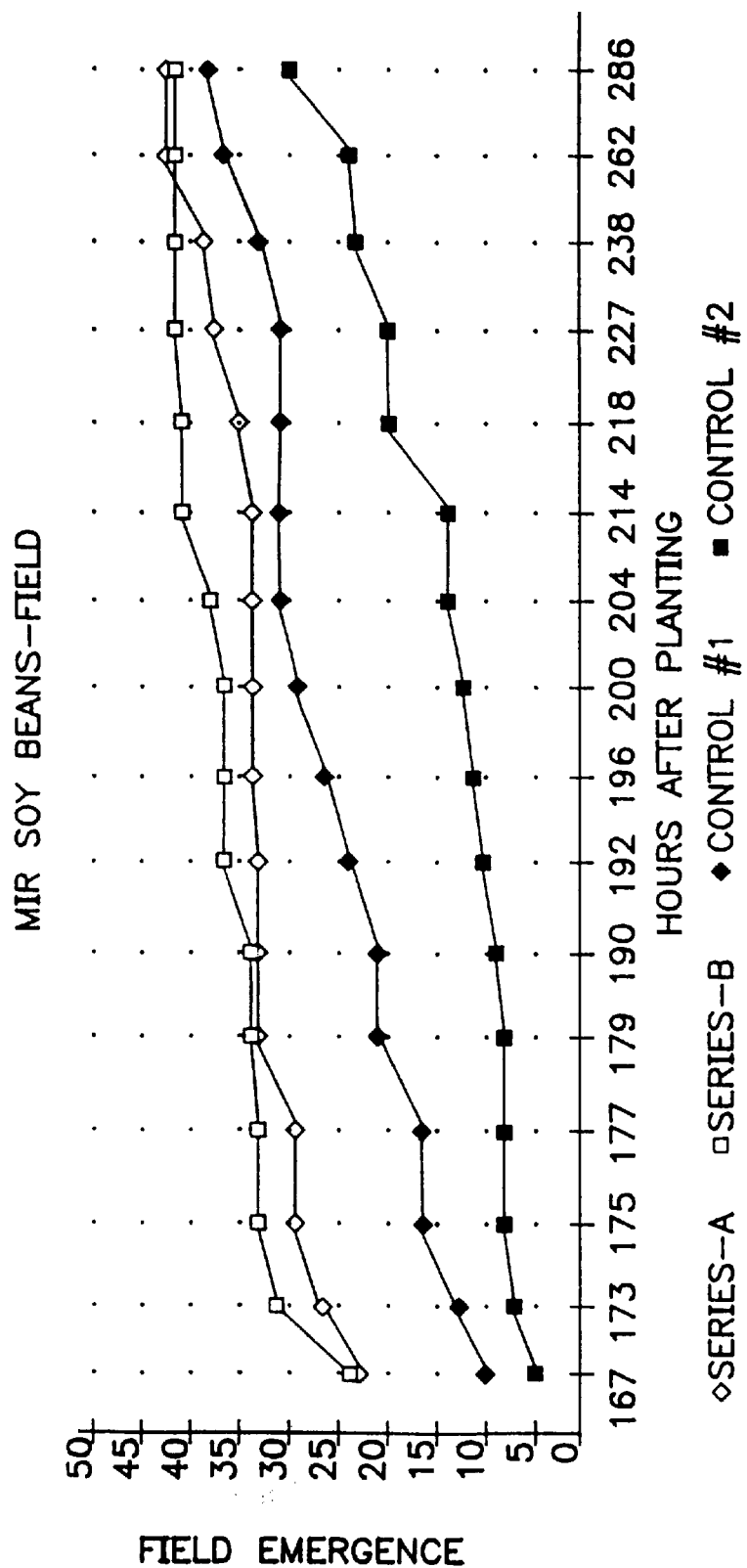

FIG. 8A is a graph showing 1995 field emergence rates in avalanche-exposed soybeans versus two control series. The seeds were Var. PS-202 (total of 48 seeds per test series). Series A: 5 kV, 5 min. Series B: 10 kV, 5 min. The seeds were stored for 86 days after treatment before planting.

Figure 8B:
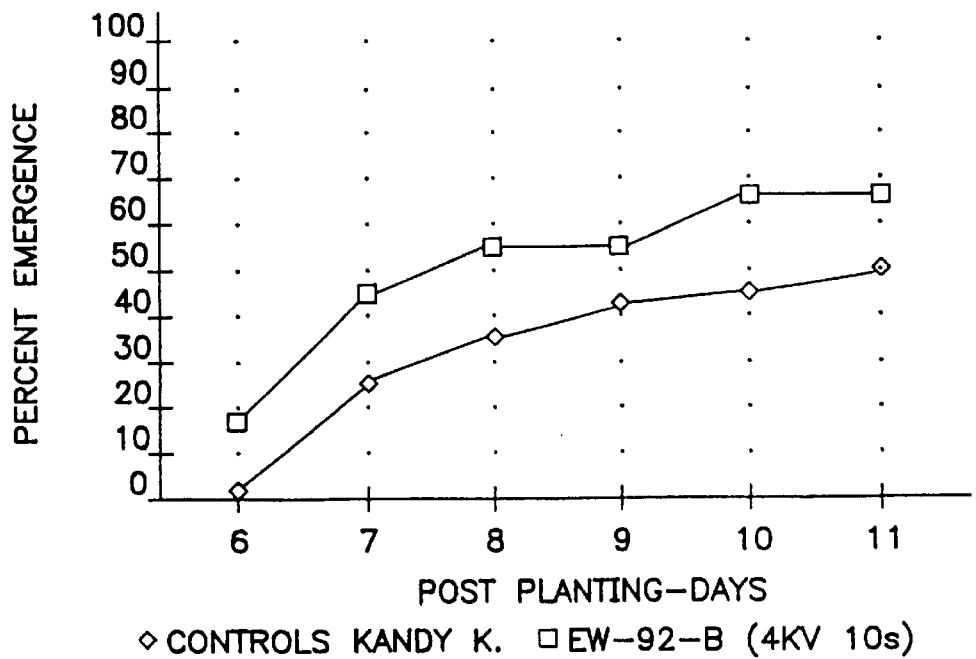
Figure 8C:
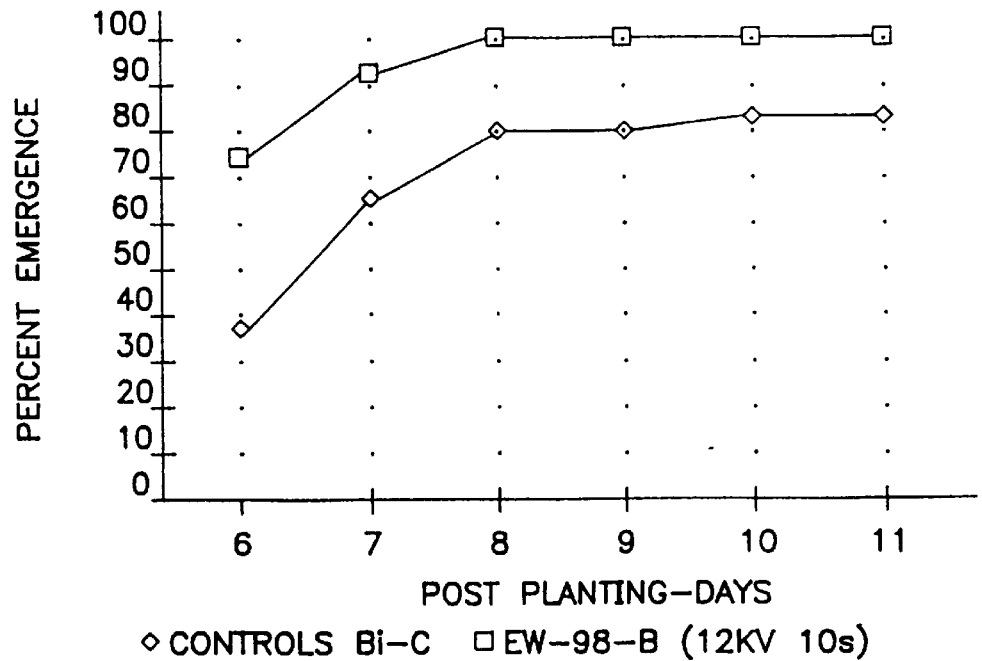

FIG. 8B and 8C are graphs showing 1995 field emergence rates in two varieties of avalanche exposed sweet corn seed versus their controls. The seeds were stored for 56 days after treatment before planting.

Figure 9A:
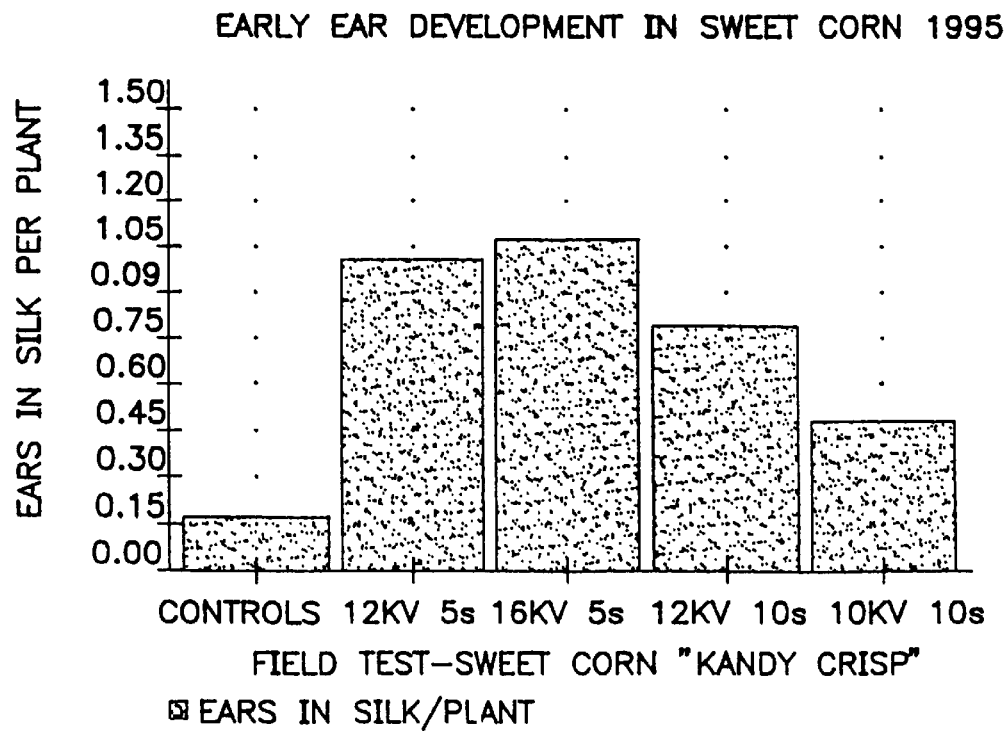
Figure 9B:
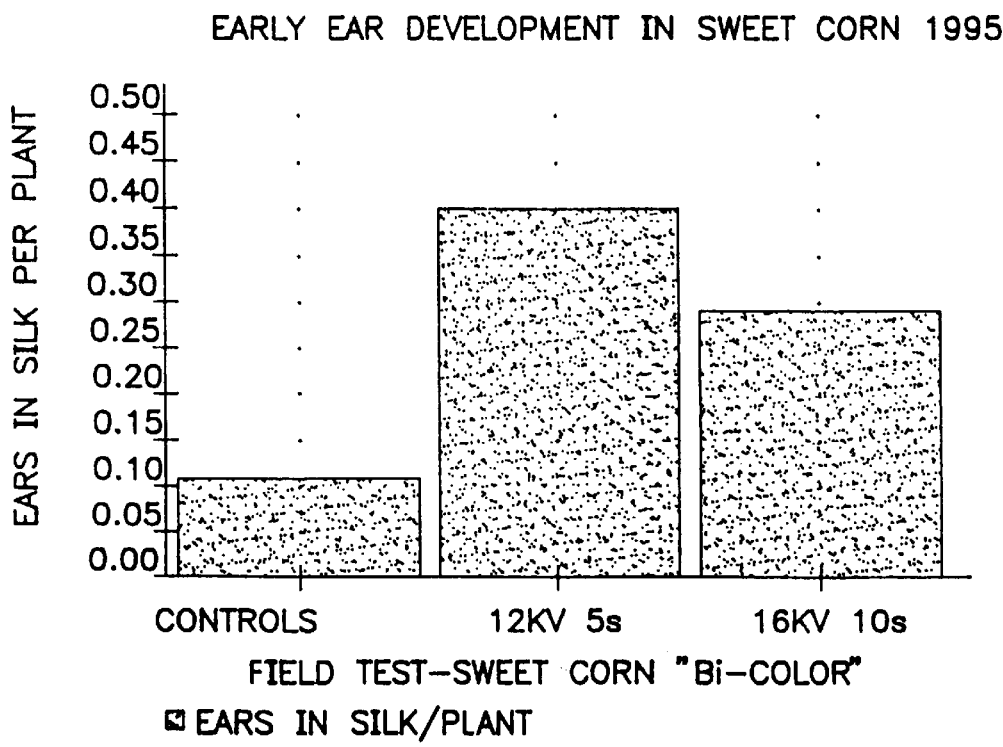

FIGS. 9A and 9B are graphs showing fruit or ear development in two varieties of 1995 field-grown sweet corn versus their controls. The seeds were stored for 56 days after treatment.

Figure 10:
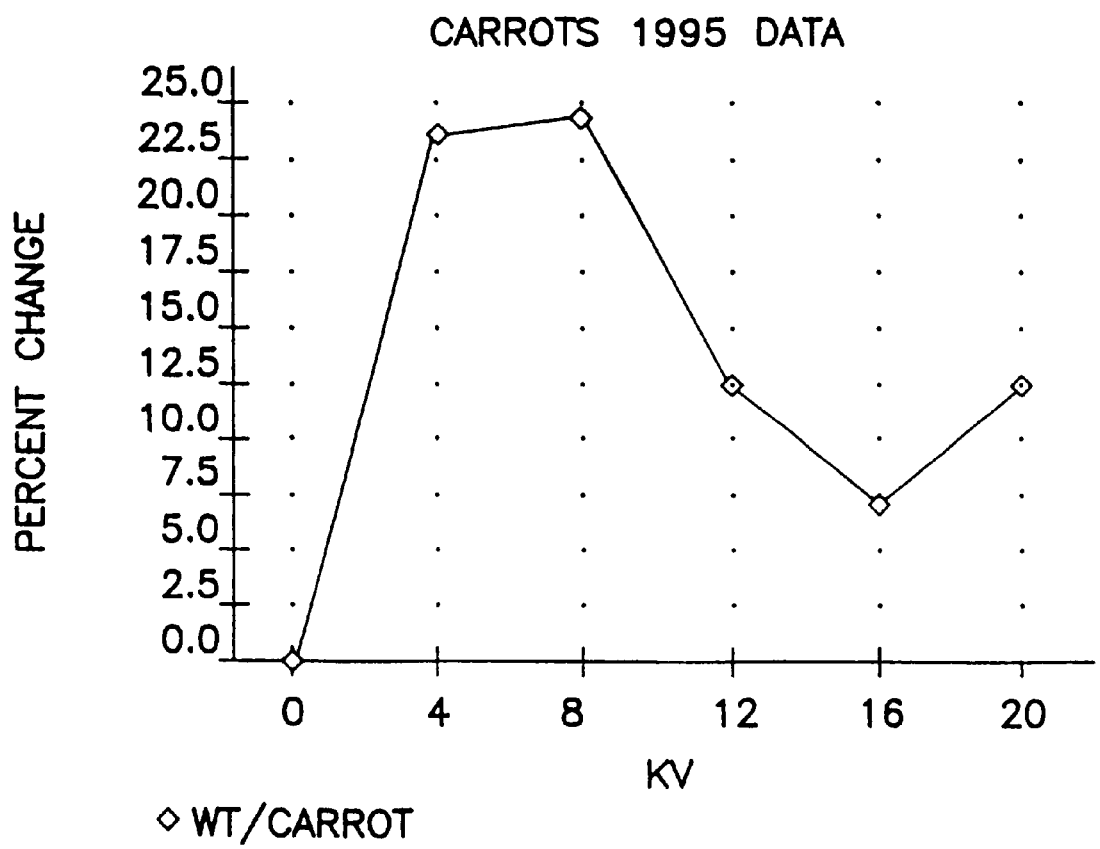

FIG. 10 is a graph showing carrot foliage yields in 1995 as a function of avalanche-inducing voltages. The field plot data is based on percent change in fruit relative to controls. Each point is a mean of a series of seeds exposed at 10 sec., 30 sec., 5 min. and 30 min. at the kv level indicated. The seeds were stored for 81 days before planting.

Figure 11:
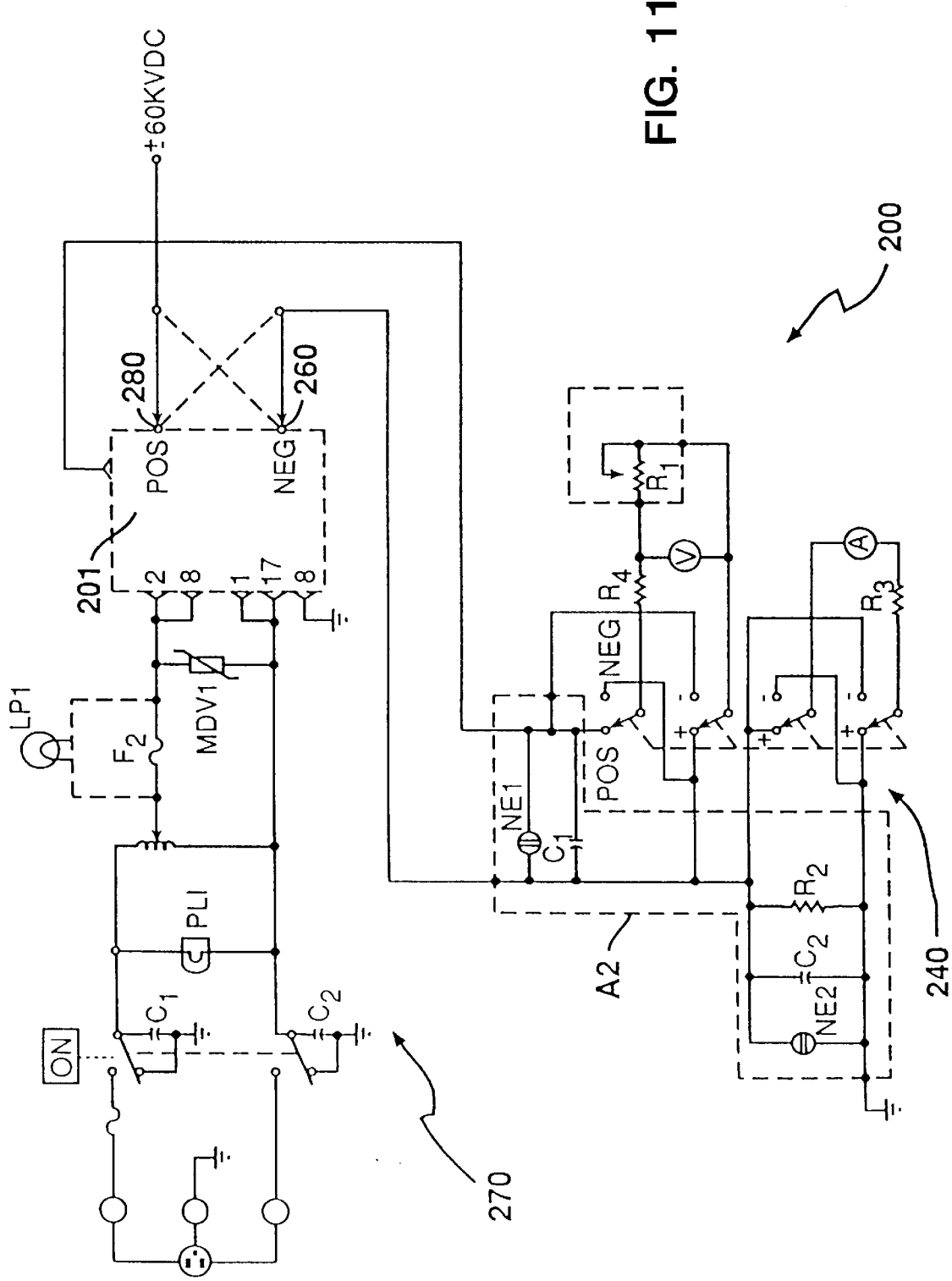

FIG. 11 is a circuit diagram 200 in box 20 of apparatus 10 for producing the spontaneous organized electron-ion avalanche pulses.

Figure 12:
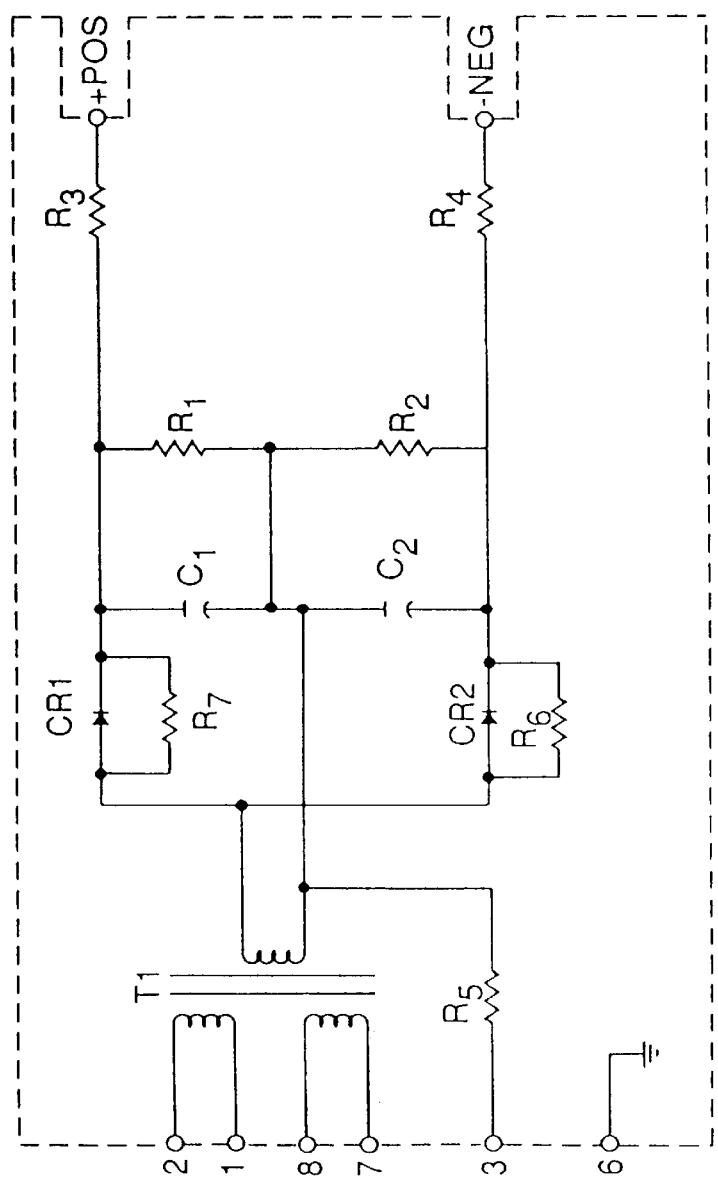

FIG. 12 is a circuit diagram for a power pack nodule 201 as shown in FIG. 11 in circuit 200 with the organized electron avalanches used in the method of the present invention.

Figure 13:
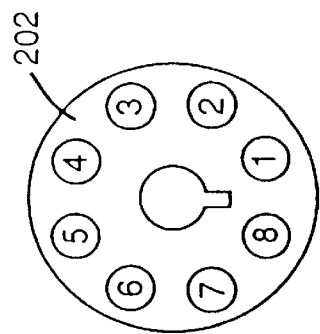

FIG. 13 is a connector for the power pack nodule 201 of FIGS. 11 and 12.

Figure 14:
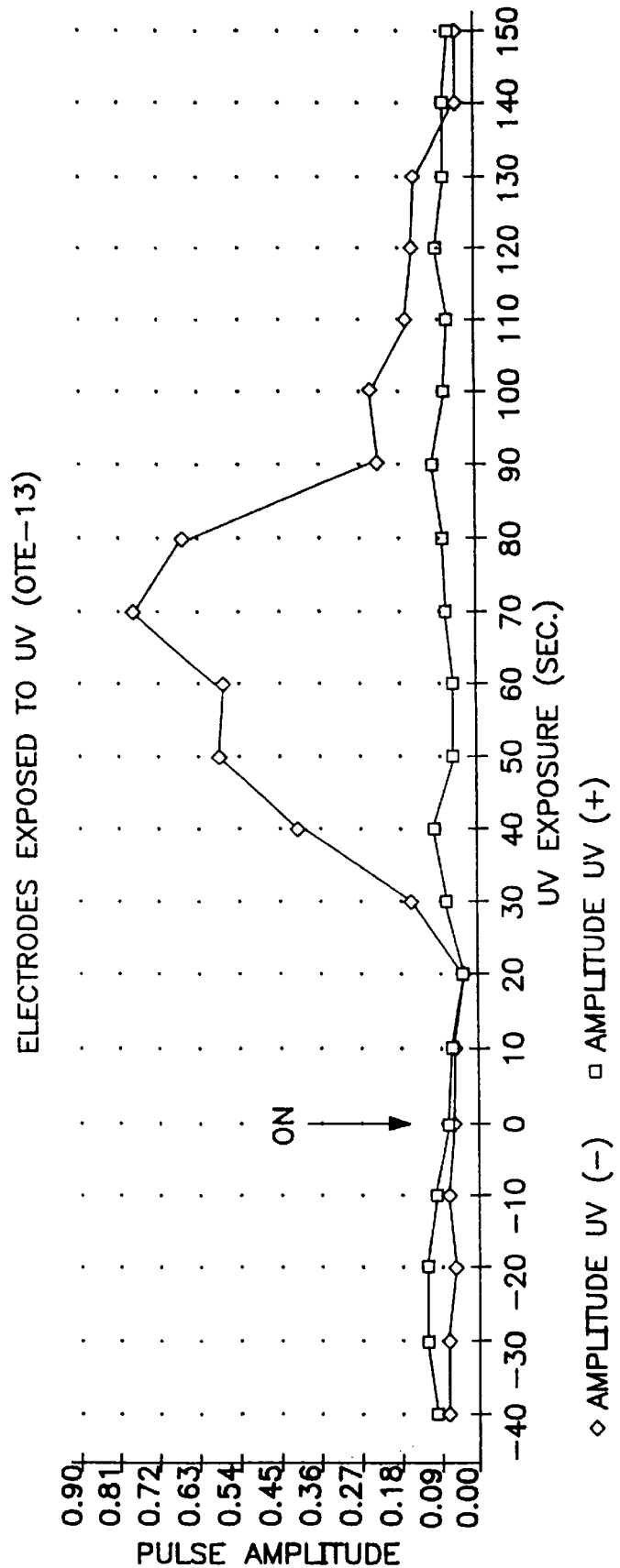

FIG. 14 is a graph showing changes in avalanche pulse amplitude as a result of photon-released electrons generated by ultraviolet light exposure at the cathode. There is no effect from exposing the anode, as we would expect from theoretical considerations.

Figure 15:
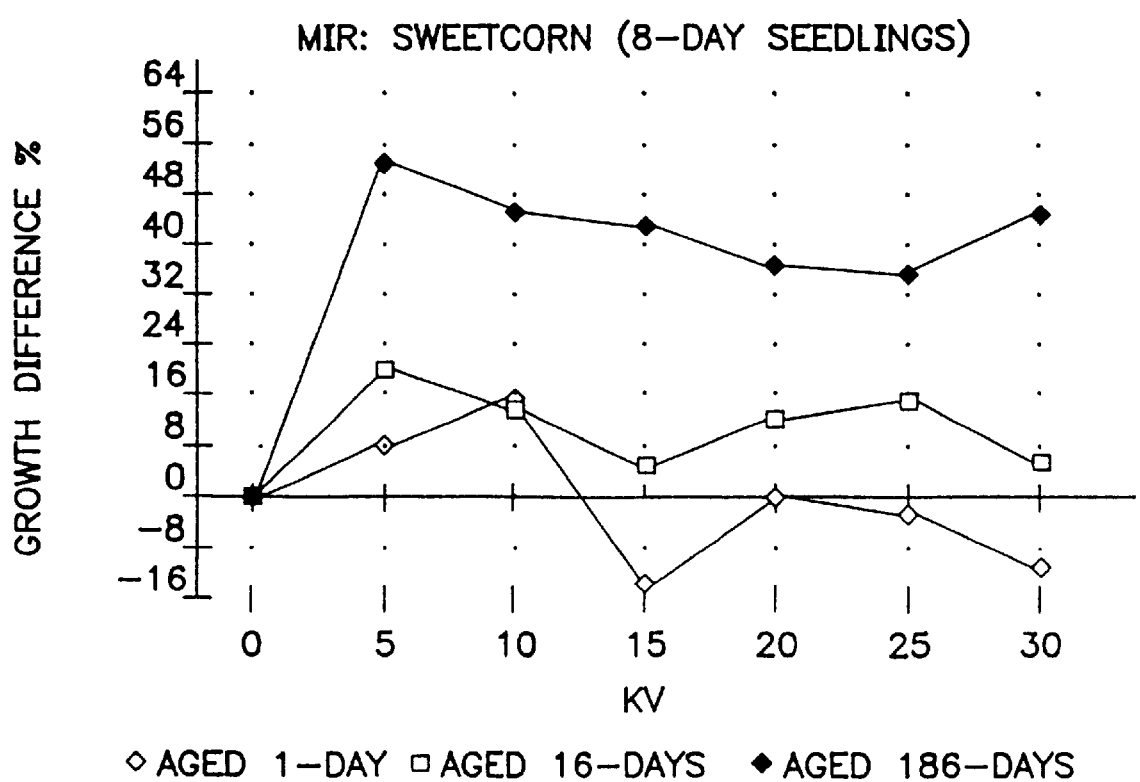
Figure 16:
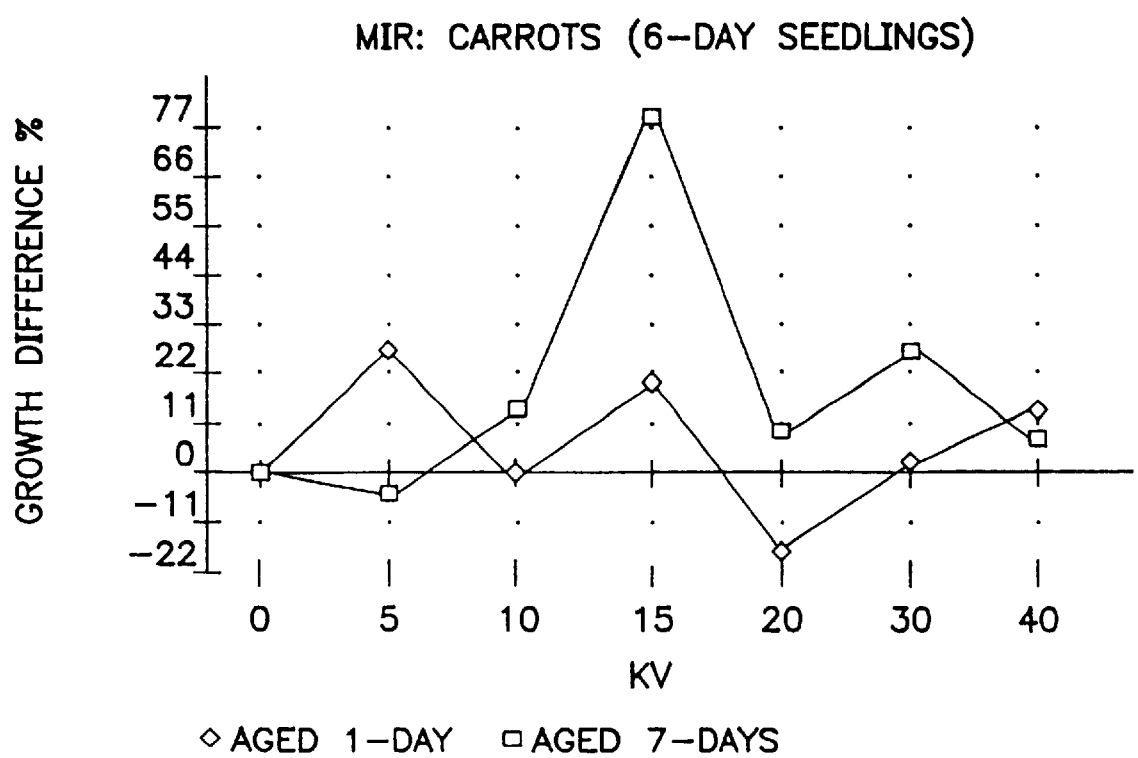
Figure 17:
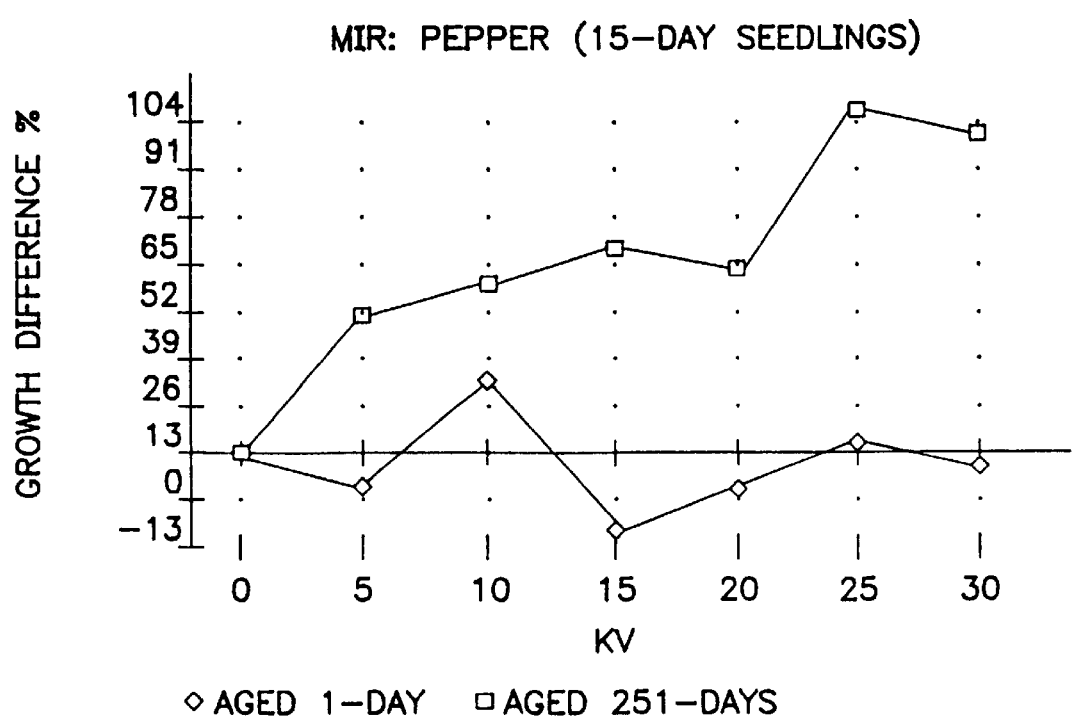

FIGS. 15, 16 and 17 are graphs showing the results of aging of the seeds for sweet corn (G18-86), carrots, pepper and oats with an exposure time of 25 seconds.

Figure 18:
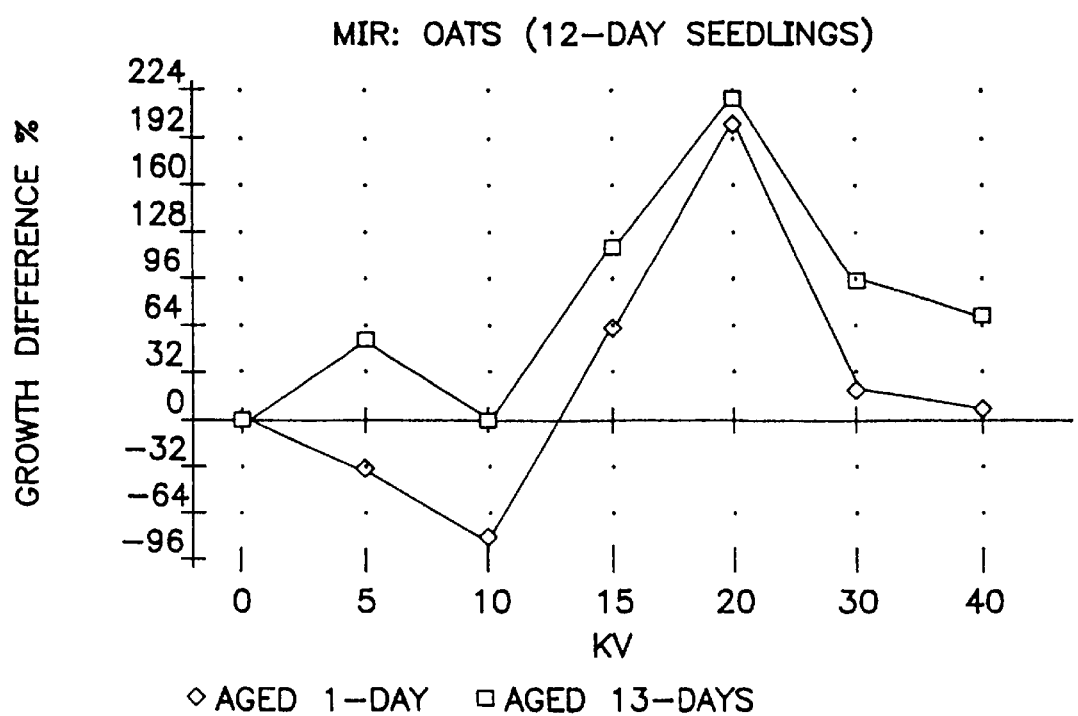

FIG. 18 is a graph showing the results of treating seeds in the panicle.

DESCRIPTION OF PREFERRED
EMBODIMENTS

The present invention relates to a method for treating a seed to enhance growth characteristics of the seed which comprises: providing the seed between a pair of spread apart electrodes as an anode and a cathode having a gap between them and with seed on or adjacent to the anode; applying a direct current (DC) voltage to the anode and the cathode using a power supply with an output voltage with an impressed alternating current AC ripple on the output voltage so as to produce self-organized, or pulsed avalanches of electrons moving from the cathode towards and into the seed between the anode and cathode or on the anode for a period of time which enhances the growth characteristics of the seed; and storing the seed for a period of time before planting sufficient to allow the seed to provide the seed with the enhanced growth characteristics.

The present invention also relates to a seed produced by providing a space between an anode with the seed and the cathode, exposing the seed to pulsed avalanches of electrons produced by applying a DC voltage, with an AC ripple impressed upon the DC voltage, to spaced apart electrodes using a power supply with an impressed AC ripple in the output voltage to produce self-organized pulsed avalanches of ion-electrons which move towards and into the seed, and then storing the seed before planting.

The present invention also relates to a plant produced from a seed produced by exposing the seed to pulsed avalanches of electrons produced by providing spaced apart electrodes which are an anode and a cathode with the seed between the anode and cathode or on the anode, applying a DC voltage with impressed AC ripple to the spaced apart electrodes to produce self-organized avalanches of electrons which move towards the anode and into the seed before planting.

The present invention also relates to an apparatus for detecting the presence of pulsed avalanches of electrons in an apparatus for treatment of a seed which comprises: a solenoid coil with multiple turns which is adapted to be positioned adjacent to a pair of spaced apart electrodes including an anode supporting the seed; and detection means for detecting an induced current in the coil.

The present invention relates to an apparatus for treating a seed to enhance the growth characteristics of the seed which comprises: a pair of spaced apart electrodes as an anode and as a cathode having a gap between them wherein the seed is to be supported on or adjacent to the anode; voltage generating means for simultaneously supplying a direct current (DC) voltage to the anode and the cathode using a power supply with an output voltage with an impressed alternating current AC ripple as the output voltage so as to produce organized, pulsed avalanches of electrons moving from the cathode towards and into the seed on the anode for a period of time which enhances the growth characteristics of the seed; and coil means with multiple turns mounted adjacent to the spaced apart electrodes which detects pulsed avalanches of electrons; and recording means for recording the pulsed avalanches of electrons as detected by the coil means.

The present invention relates to a method for significantly improving the rate and uniformity of germination and early growth, as well as increased yield, in plants, particularly commercial crops, by a cost-effective treatment of the seeds using electron avalanches in a manner that can be reliably duplicated, and lends itself well to commercial exploitation. The method provides an apparatus for exposing seeds to organized avalanches of electrons from a flat electrode.

The seeds 13 are placed directly on top of a horizontal, flat aluminum (or other metal) plate or electrode 11 which is an anode spaced from an electrode 12 which is a cathode so that the electrode 11 is the bottom most of the two parallel electrodes 11 and 12. Alternatively, the seeds can be placed on a non-conducting screen 22 (FIG. 5) elevating them above the anode electrode 11. For all results listed here, the elelectrodes 11 and 12 used were round and 30 cm in diameter. Other shapes and sizes of electrodes can be used, though this may change the effective voltage levels. The electrodes 11 and 12 are supported by legs 14 and 14A made of a dielectric material. The bottom electrode 11 can take a variety of forms, such as a metal conveyor belt (not shown).

A high-voltage DC power supply 20 providing positive current is connected to the bottom electrode (anode) 11, while the top electrode 12 (cathode) is grounded. Improved results are obtained if the DC power supply contains an organized 60 or 220 Hertz ripple in the DC. Other than such an AC trace and its resultant ripple, there is no other oscillation of the DC current. This distinguishes the apparatus from prior art systems which use a voltage oscillator, usually in the megahertz range or higher.

Due to conductivity of the air between the electrodes 11 and 12, organized avalanches of electrons travel from the negative electrode 12 (cathode) to the positive electrode 11 (anode). These electron avalanches register as pulses on the monitoring equipment described hereinafter. When a "clean" signal DC power supply is used, both the frequency and amplitudes of the ion-electron avalanches are lower and more irregular. When a power supply with AC ripple is used, the avalanches form in regular self-organized, discrete pulses. These avalanche pulses commonly occur in the 0.1 to 30 Hz range between the electrodes 11 and 12 and are a product of voltage gradient and conductivity of the air between the electrodes 11 and 12, not of an artificial oscillator. The term "self-organized" means that there is a discharge between the electrodes 11 and 12 dependent upon the voltage and the environmental conditions between the electrodes 11 and 12.

The best results have been obtained when the electrodes 11 and 12 are supported on dielectric legs 14 on a plastic-topped table 16 and the bottom electrode 11 is grounded to the tabletop by a feedback loop 15 of a conductive metal. When the feedback loop 15 is added, the same electrode system produces pulses of very similar frequency to those obtained without the loop, but of significantly increased amplitude. The reason for this is that the table top 16 appears to function as a feed-back loop type of capacitor.

It has been found that an avalanche inducing voltage improving the seeds of some plant varieties was ineffective or actually harmful to seeds of other varieties. Likewise, the duration of the seed's exposure to the electron avalanches is important and variable. The diagnostic process to select the best times and voltages is also important. Finally, the waiting period before planting, and considerations of moisture in the air and seed temperature are important. The present method works well on seeds dried to normal levels for commercial storage and at temperatures above 40° C. Monitoring apparatus, described later, can be used to adjust for altered air conductivity due to changes in relative humidity.

Figure 1A:
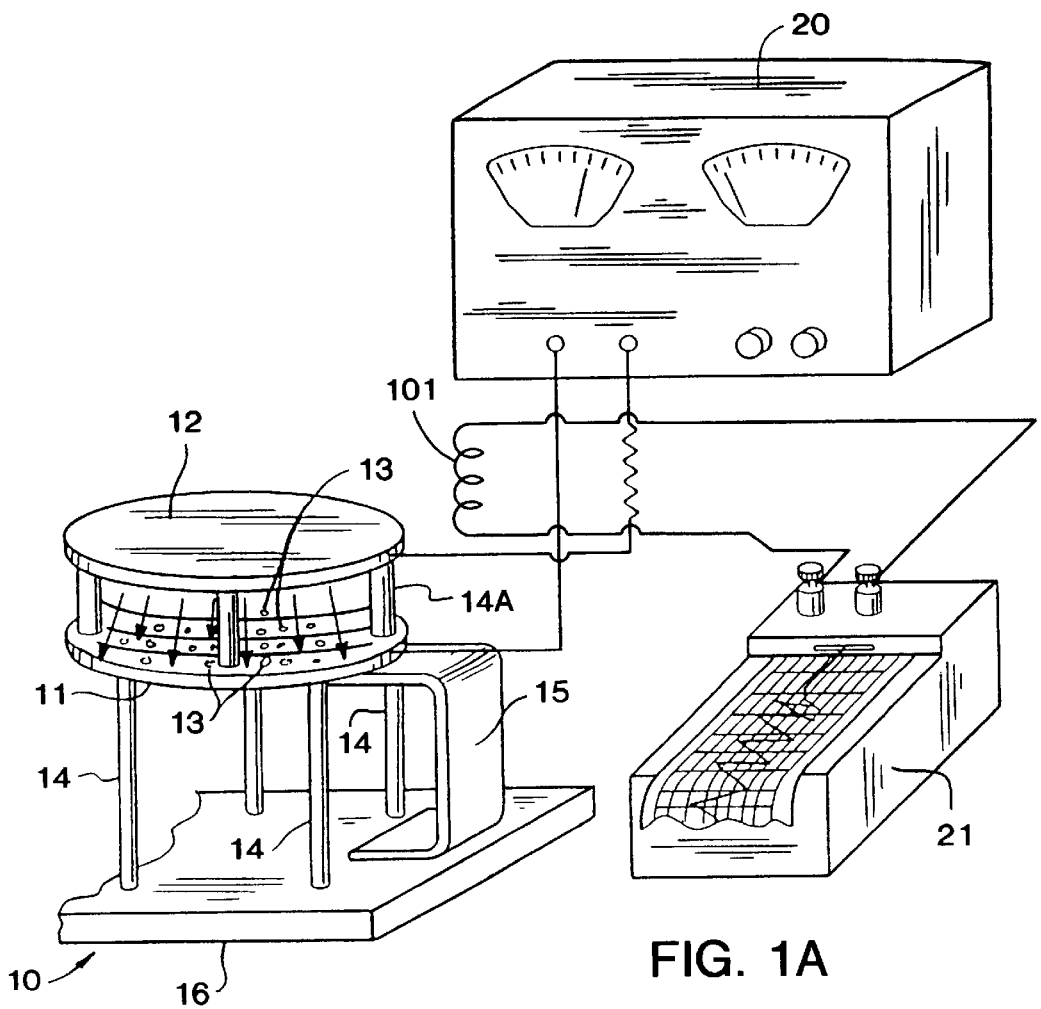
FIG. 1A is a schematic view of the apparatus of the present invention for producing controlled, spontaneous, electrostatic pulses which form the organized electron avalanches between an anode electrode 11 supporting seeds 13 and a cathode electrode 12.

The method of the present invention is referred to as Molecular Impulse Response, or MIR. A specific type of impulse from an electron produces a molecular response in the seed which ultimately results in significantly-improved seed performance, when it is applied in the following manner, including but not limited to:

A.) Electrodes and Power Supply: Using a spacing between electrodes 11 and 12 (preferably 8 cm although other spacings, preferably between about 1 and 20 cm, can be used but will alter the effective voltages) and inducing a voltage gradient between the electrodes of about 2 kV or more (other voltages can be used up to, but below, the electrical breakdown voltage in air corona discharge) results in the production of organized electron avalanches which take the form of sharp, regular electrical conductivity pulses of relatively uniform amplitude in the air between the electrodes 11 and 12 (as traced on a chart recorder system 21 as shown in FIG. 1A) Such spontaneously organized electron avalanches have been described in the scientific literature, most notably by Nasser, as examples of a low density, low energy plasma in air at ambient pressure. (Source: E. Nasser, "Fundamentals of Gaseous Ionization and Plasma Electronics", Wiley-Interscience, New York, pages 209 to 217 (1971)).

Figure 1B:
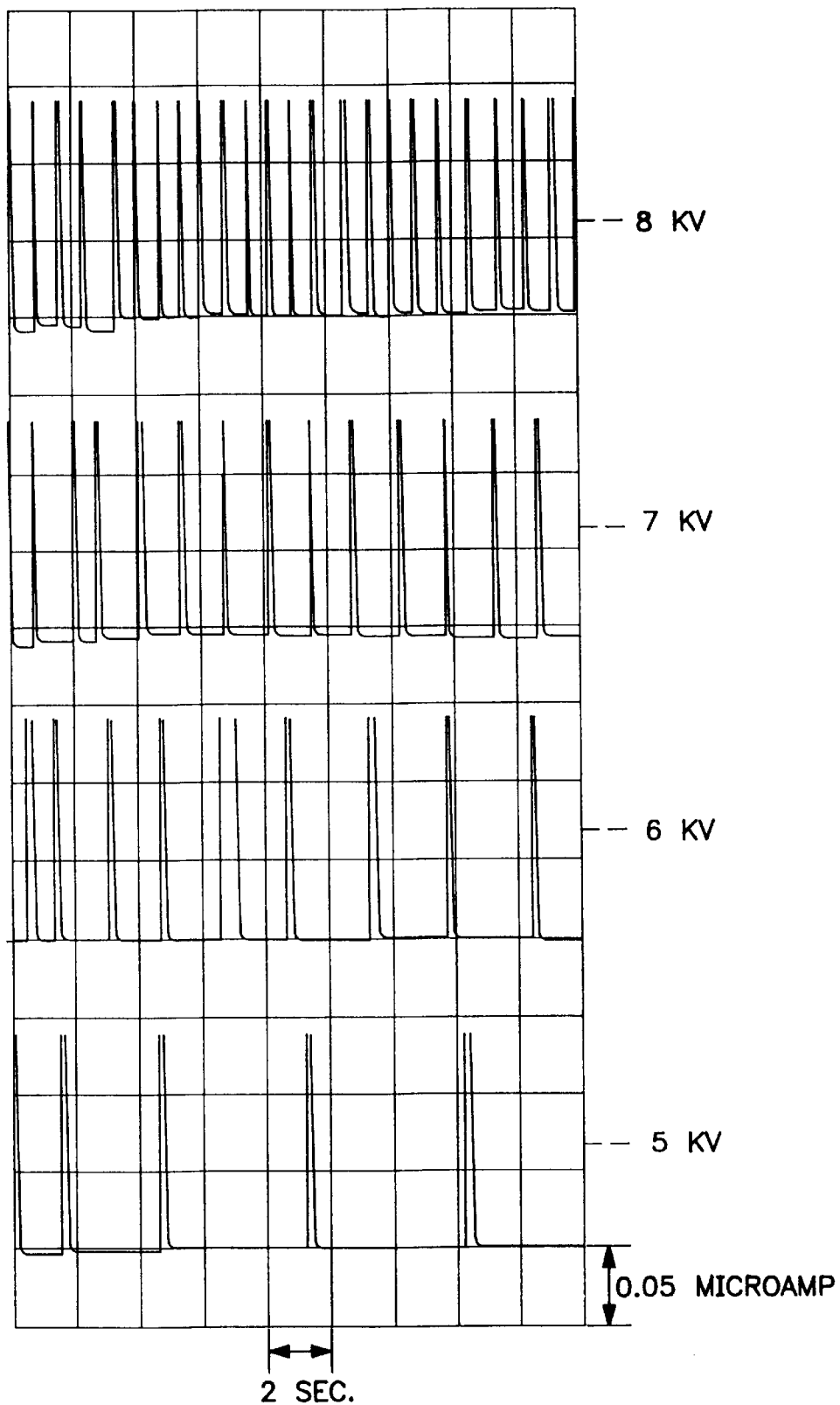
FIG. 1B is a charted graph showing organized electron avalanches produced in the apparatus of FIG. 1A with different DC voltages (relative humidity 26%; p =1009.3 mb).

The frequency of the avalanche pulses rises spontaneously with increasing voltage (see FIG. 1B). This is different from the oscillating electric field employed by the prior art in which the frequency is fixed artificially and remained the same unless human intervention changed it. This difference is at the heart of the present invention because it is not oscillation of the electric field which produces the desired results but these spontaneous, organized avalanches of ion-electrons produced between the electrodes 11 and 12 in air which elicit the Molecular Impulse Response.

Use of a pure DC power supply, with no AC ripple, results in electron avalanches with significantly less pulsing and regularity. Exposure of seeds to these pulses results in a lower seed performance than those exposed to a DC power supply with an AC ripple. Furthermore, results are difficult to consistently reproduce when an AC ripple is absent. Thus it is not merely exposure to an electric field which produces the beneficial results claimed here, nor is it exposure to any type of electron avalanches. The seeds must be exposed to the sharp, regular, uniform or organized electron avalanches as shown in FIG. 1B for best results.

B.) Diagnostic Procedure: Different voltages (generally between 2–20 kV) and different time exposures (from seconds to minutes) produce the best results with different varieties of seed. The optimal parameters are selected for each seed by exposing them at a range of voltages for a range of times, and comparing the results by germination and/or growth and/or yield tests, as well as by redox measurements.

A redox diagnostic procedure allows the achievement of significant improvements in a wide variety of seed/plant types. This diagnostic procedure is necessary because a variety of seed which is positively effected at a high (20 kV) or low (5 kV) voltage may be effected negatively by a medium (15 kV) voltage. Conversely, seeds which do well at a low voltage may do poorly at a high voltage and vice versa.

It has been found that the seeds should be stored at 40° F. to 80° F. If the temperature is too low then no result is achieved.

It will be appreciated that the seeds can be positioned on a non-conductive screen 22, such as fiberglass, between the electrodes 11 and 12 as shown in FIG. 5. Preferably the electrodes 11 and 12 are round with rounded edges. The electrode preferably has a 8 to 9 cm gap and a diameter of about 30.5 cm. The seeds are placed on the electrode so as not to be touching significantly.

EXAMPLE 1

This Example shows laboratory germination tests accurately diagnosing treatment levels which produce yield increases, plus examples of how a voltage which is good for one crop produces marginal or decreased yield in another, as compared to untreated controls as shown in Table 1:

TABLE 1

| Crop Type | Best Germ. kV | Good Yield[1] kV | Marginal or Poor Yield |
|---|---|---|---|
| Tomato | 5 kV | 4, 12, 16 kV | 8, 20 kV |
| Carrot | 5 kV | 4 kV | 12, 20 kV |
| Soybeans | 8 kV | 8,12 kV | 4 kV |
| Navy Beans | 10 kV | 10, 12 kV | 6 kV |
| Bi-Color Sweet Corn | 15 kV | 16, 8 kV | 12, 4 kV |
| Kandy-Krisp Sweet Corn | 15 kV | 16, 12 kV | 4, 8 kV |
| Inbred Field Corn | | 4, 16 kV | 8, 12, 20 kV |

TABLE 1-continued

| Crop Type | Best Germ. kV | Good Yield[1] kV | Marginal or Poor Yield |
|---|---|---|---|
| Hybrid Field Corn | | 4, 12, 16 kV | 8, 20 kV |
| Cypress Rice | 15 kV | 16 kV | |

[1]Measured by fruit and grain weights.

Frequently, laboratory germination voltages were tried in increments of 5, i.e. 5, 10,. 15 kilovolts, while field tests were in increments of four kilovolts, thus producing non-exact matches. Results of a range of treatment durations have been averaged here for each voltage for simplicity.

Figure 2A:
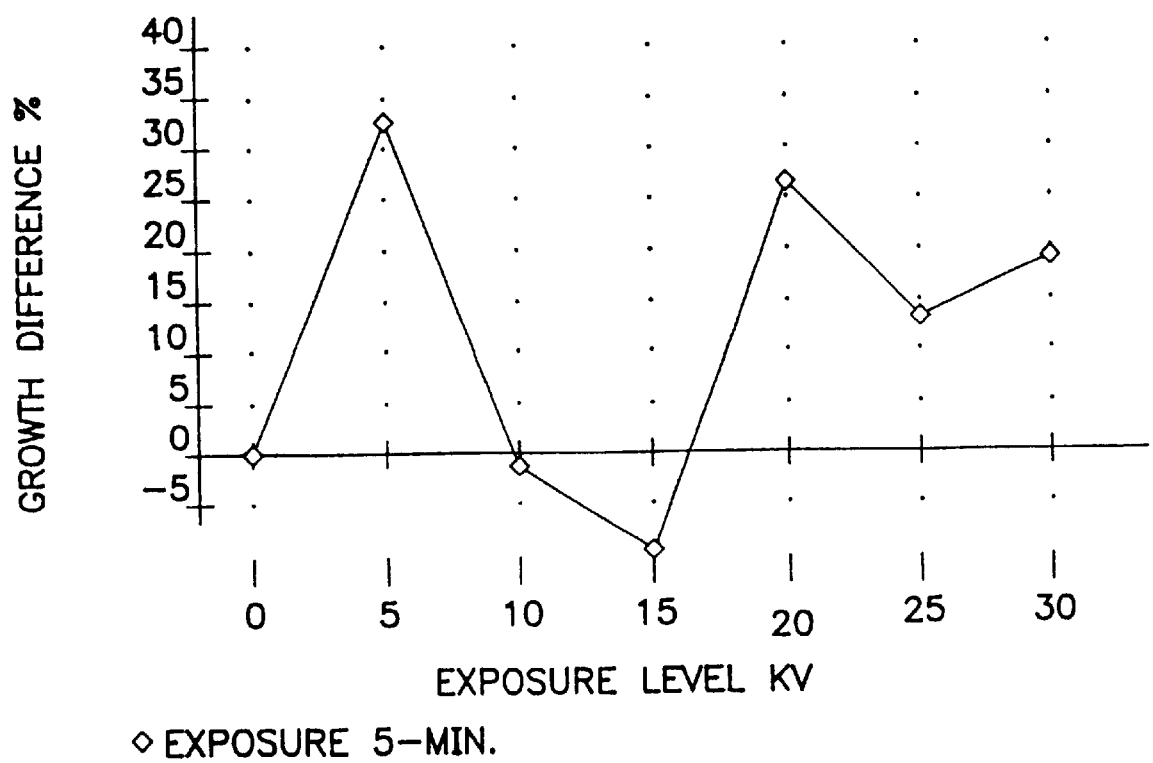
FIGS. 2A, 2B and 2C are graphs showing growth differences in tomatoes, pepper and carrot using a DC voltage for five minutes in the apparatus of FIG. 1A with seeds stored for 35 or 36 days. Germination data was taken at the 12-day growth stage and represents hypocotyl extension (seedlings placed under grow lights at 4-day development). The data was compared with two control sets in each test series.
Figure 2B:
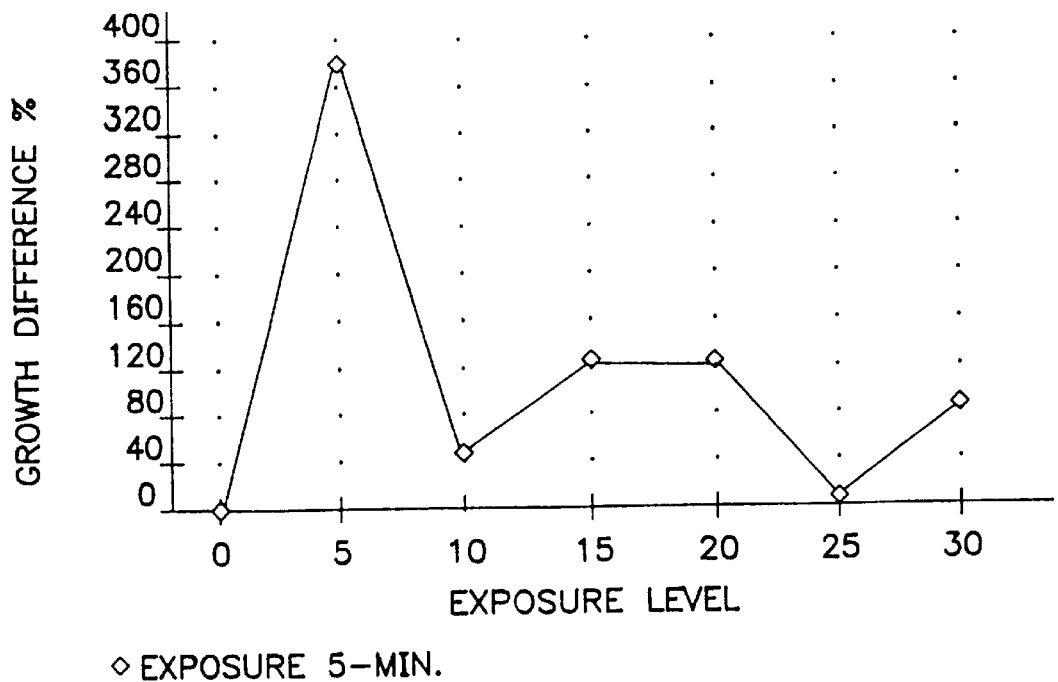
Figure 2C:
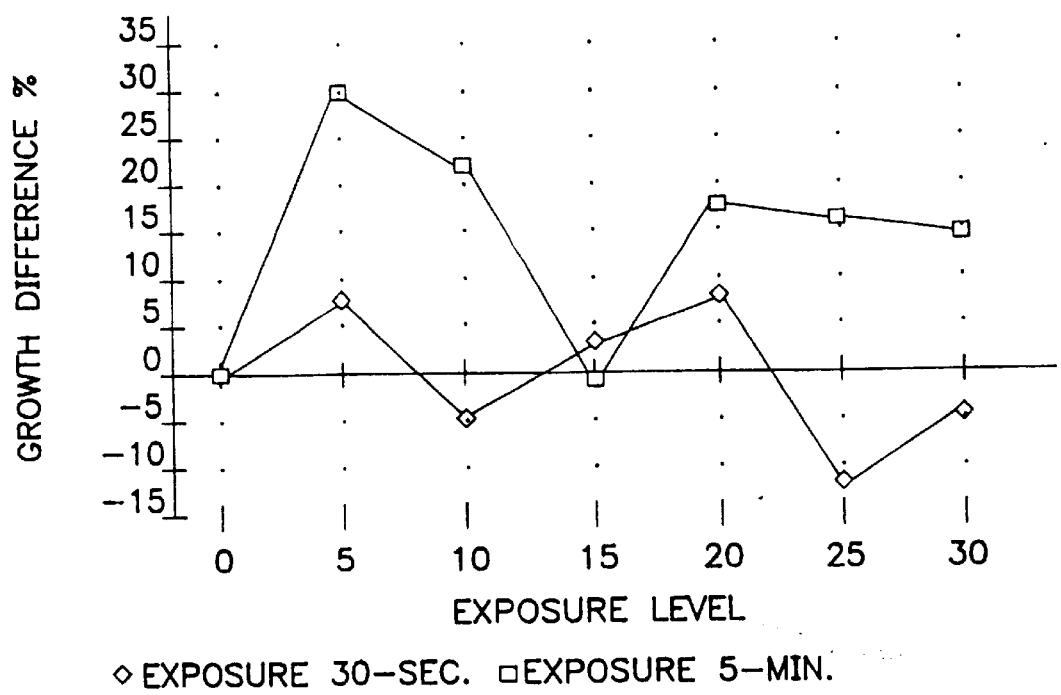

A key element of the present invention is a waiting period during which treated seeds are not germinated for a minimum of several weeks after exposure. Germination of exposed seeds before this waiting period is completed can result in no improvement in the seeds or even negative effects. Consistent, reproducible, improvements are not found with seeds planted soon after exposure. Improved effects in treated seeds have been seen as long as 18 months after treatment. There is not as yet any known upper limit to the waiting period. While the minimum waiting period varies from one seed variety to another, a minimum of 30 days has been found to be effective. The seeds of FIGS. 2A to 2C were stored for 35, 35 and 36 days respectively.

Figure 3A:
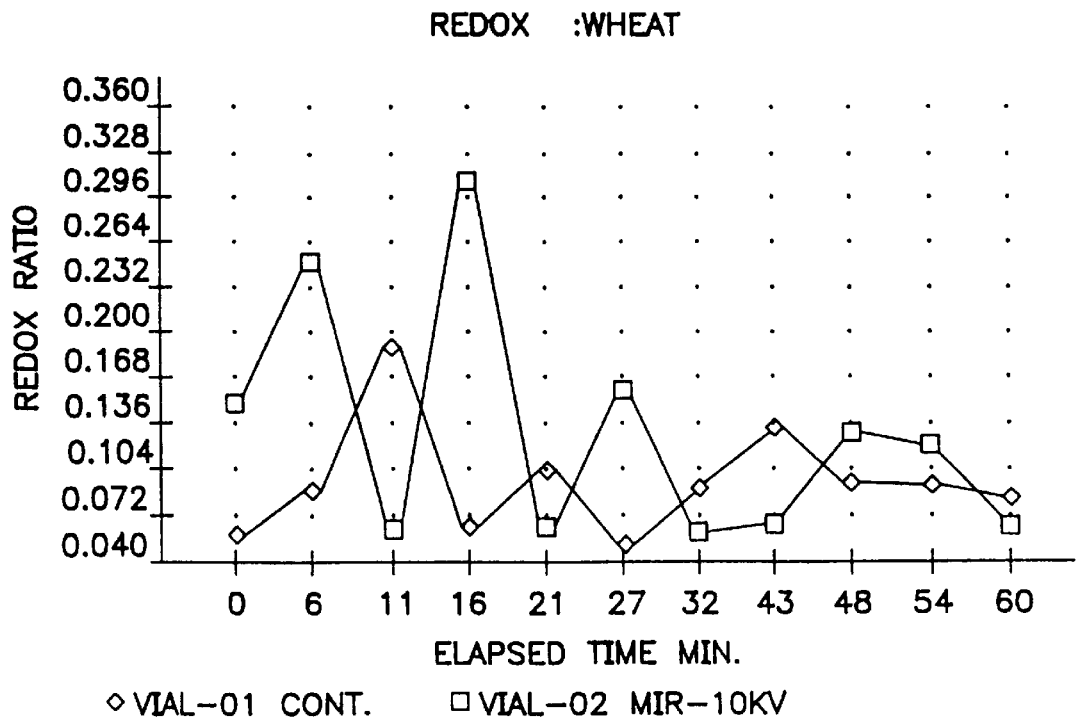
FIGS. 3A and 3B are graphs showing redox ratio (ratio of active anions to cations) changes in developing wheat and maize seedlings over a 60 minute test interval in both untreated, control seed and in seed exposed to the spontaneously organized ion-electron avalanches, with avalanche exposure of 30 seconds at 10 kV (FIG. 3A) and 20 kv (FIG. 3B) The seeds were stored for eight (8) days. The leaf tissue between electrodes 11 and 12 was tested after 12 days under a grow light.
Figure 3B:
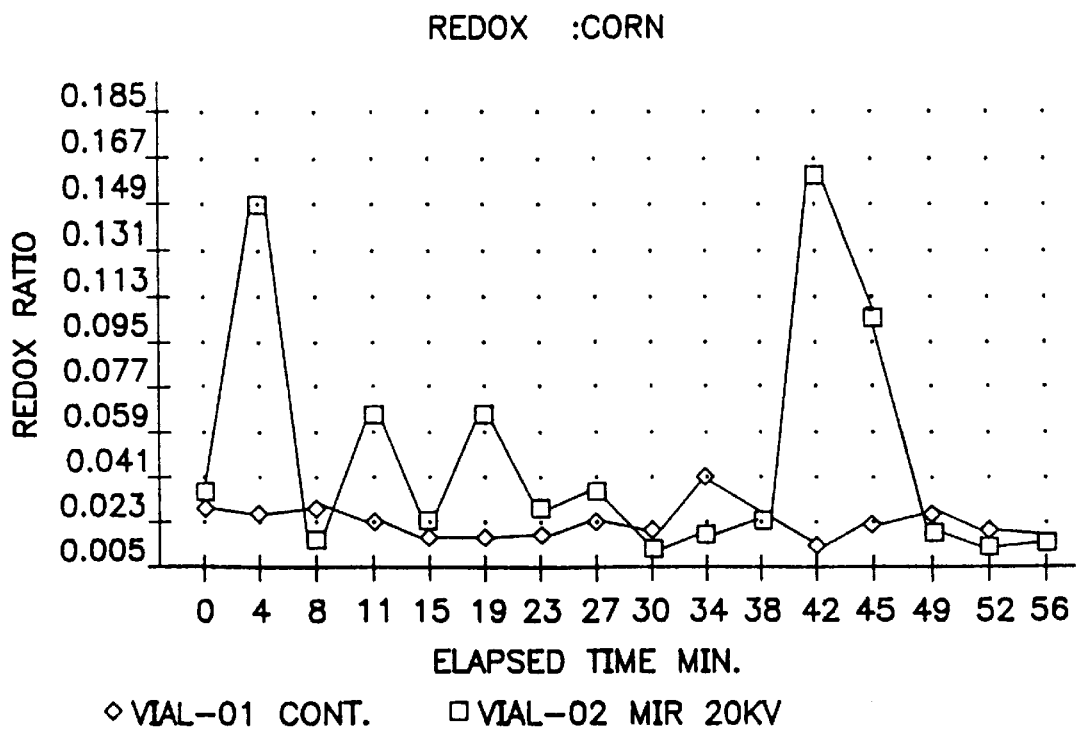
Figure 4:
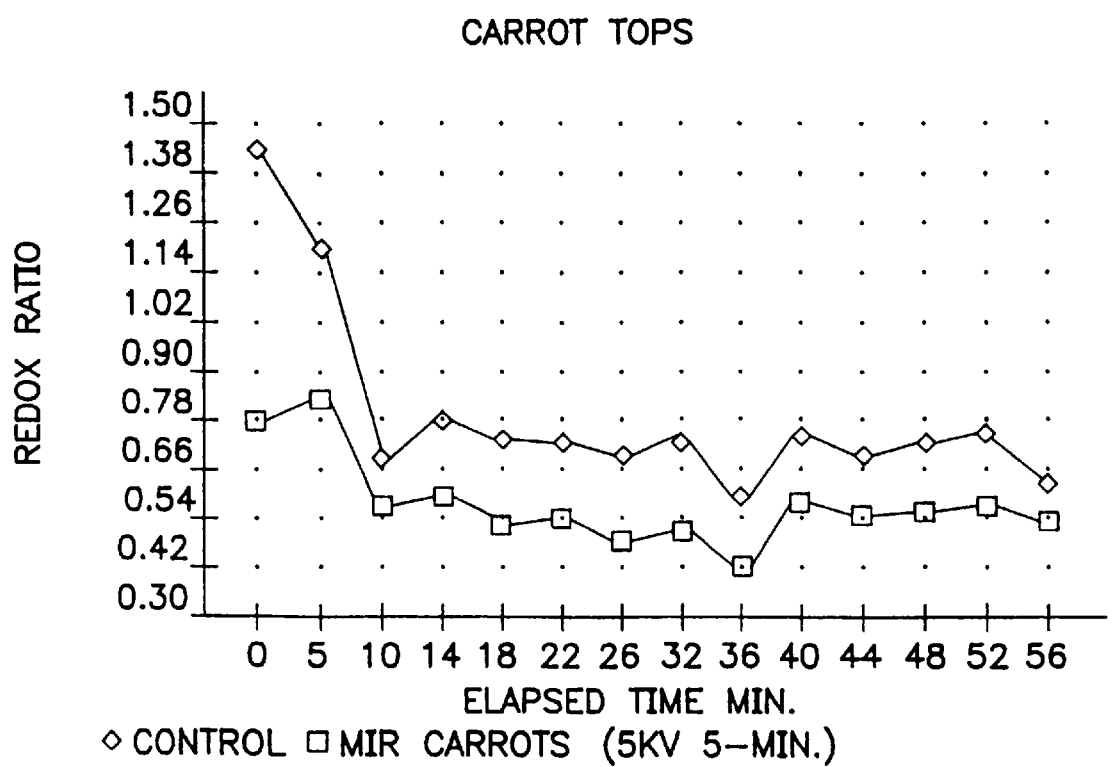
FIG. 4 is a graph showing redox ratio changes in mature, field grown carrot foliage from both untreated control seeds and seeds exposed to ion-electron avalanches at 5 kV for 5 minutes and stored for 81 days before planting. Redox Ratio.

The redox ratio is a measure of temporal variations in respiration as measured by changes in oxidation/reduction activity in seedlings grown from treated seeds. Increased phase amplitudes of redox cycles, indicative of increased rates of respiration and free radical activity, have been consistently measured in 10–12 day seedings grown from MIR-treated seeds (FIGS. 3A and 3B). Many studies have suggested that alterations in redox ratios are linked with growth responses in biological organisms. (Levengood, "Bioelectrochemistry And Bioenergetics, 19 461–476 (1988); also Allen and Balin, "Free Radical Biology and Medicine" Vol. 6, pp. 631–661 (1989); A. Sakamoto et al., FEBS Letters, Vol. 358 pp. 62 (1995)). Whether or not this is in fact the mechanism of the present invention, alterations in redox ratios have been seen to be linked with improved growth performance in MIR-treated seeds, including eventual increases in final yield. In the green seedling autotrophic stage, redox levels of seedlings grown from MIR-treated seeds are lower than in untreated seedings as shown in FIG. 4, consistent with the hypothesis of higher levels of antioxidants present which deactivate free radicals and thereby lower redox ratio levels.

Measurements were made according to the procedure set forth in Levengood, Bioelectrochemistry And Bioenergetics, 19 461–476 (1988). Detection of the above-mentioned free radical alterations can be used as a means of quality control for MIR operations. This monitoring or quality control can serve as a rapid check that the desired effect is being achieved in the treated seeds, without resorting to time-consuming growing of the seeds. This redox ratio analysis makes commercial scale operations reliable and dependable.

From several hours to several days after treatment, MIR seedlings display raised redox ratios, indicating a burst of free radicals within the cells formed by the impact of the ion-electron avalanches. Seeds experience activation of cellular anti-oxidant defenses and consequently have lowered redox ratios. In dried seeds this process moves slowly, as do all metabolic processes in quiescent seeds. Seeds which have been treated at an effective voltage and for an effective time will, during storage, experience a redox level shift as cellular anti-oxidant defenses, such as Superoxide Dismutase (SOD) and others, deactivate the free radicals. In maize, for example, cells have been known to produce more SOD than needed to disable the free radicals present. Gail L. Matters and John G. Scandalios, "Effect of the free radical-generating herbicide paraquat on the expression of the superoxide dismutase (Sod) genes in maize", Biochemica et Biophysica Acta 882 p. 33 (1986) observed 54% increases in SOD levels but only a 40% increase in SOD activity, in response to a burst of superoxide radicals. Thus the resulting surplus of anti-oxidants lowers the normal levels of free radicals in seeds and in mature, developing plant tissue the MIR treated plants have lower redox ratio than in the untreated controls as shown in FIG. 4.

As shown in FIG. 5, the spatial drift of the MIR pulses outside the electrodes 11 and 12 can be examined by stationing an experimental probe coil 101 near the electrodes 11 and 12. A linear chart recorder 21 is used to detect the induced current in coil 101. The electron avalanches drift laterally from between the electrodes 11 and 12 and through an electrostatic-magnetic coupling induce a magnetic field in the coil 101, which in turn generates a potential in the millivolt range. With the coil 101 placed directly across one channel of a dual channel chart recorder such as recorder 21 in FIG. 1A and the MIR system across the second channel, one can examine the effectiveness and form of the pulses in action. For example, the set of curves in FIG. 6 show the magnetically induced and MIR pulses from the coupled system. The coil 101 usually has 10,000 to 100,000 turns, preferably 80,000 turns.

As pointed out by H. Raether ("Electron Avalanches and Breakdown in Gasses", Butterworth & Co. Ltd., U.K. 1964) one reliable criteria to know whether an observed current pulse can be identified with an avalanche process is to compare the form of the avalanche pulse with the induced magnetic component. From the basic theory of electron avalanche formation one should find that the induced magnetic component H (expressed here as coil 101 potential) is directly related to ln(i), where i is the amplitude of the avalanche current pulse in the MIR system. The experimental data in FIG. 7 confirms (r=0.89; P<0.05) that these are electron avalanches.

EXAMPLE 2

When the above steps are used together as part of a coherent process to treat the seeds in the aforementioned manner, the following results have been achieved in a variety of crops in both laboratory and field tests:
1) Increased rate of field emergence. An example is shown in FIG. 8A for *Glycine max*. Var. PS-202 and in FIGS. 8B and 8C for two varieties of *Zea mays* sweet corn.
2) Increased rates of plant growth and plant size uniformity.

EXAMPLES 3 AND 4

Examples of the MIR effect in sweet corn are disclosed in Table 2 and 3 below. The data were taken at 52 days development within field test plots. The seeds were stored for 56 days.

Variety-"Kandy Krist"

TABLE 2

| | Plant heights (cm) | | | | |
|---|---|---|---|---|---|
| Series | ave. | sd | N-plants | Coeff. of Var. | kV-level |
| Controls | 113.2 | 29.8 | 49 | 26.3% | None |
| 5 sec. | 145.2 | 11.3 | 31 | 7.8% | 12–16 |
| 10 sec. | 134.8 | 26.7 | 37 | 19.8% | 12–16 |

Variety "Bi-Color"

TABLE 3

| | Plant heights (cm) | | | | |
|---|---|---|---|---|---|
| Series | ave. | sd | N-plants | Coeff. of Var. | kV-level |
| Controls | 109.6 | 36.3 | 81 | 33.1% | None |
| 5 & 10 sec. | 126.6 | 28.4 | 43 | 22.4% | 12–16 |
| 5 min. | 123.2 | 28.4 | 36 | 23.1% | 12–16 |

EXAMPLE 5

Increased lateral root growth which has been achieved.

Navy bean seed were treated on Sep. 30, 1992 and germinated 65 days later (20 seeds per lot) as shown in Table 4.

TABLE 4

| Voltage | Duration | 3 Day Roots | sd | Number |
|---|---|---|---|---|
| 5kV | 25 sec. | 6.26 cm | 1.64 | 20 |
| 10 kV | 25 sec. | 6.63 cm | 0.92 | 19 |
| Control | 0 | 4.54 cm | 2.63 | 20 |

EXAMPLE 6

Accelerated maturity has been achieved. Some plants grown under open field conditions from treated seed reach the harvest stage in significantly fewer days, as compared to controls. With sweet corn of two varieties, ears with protruding silk were counted 52 days after they were planted as shown in FIGS. 9A and 9B.

EXAMPLES 7, 8, 9, 10, 11, 12

Increased Yield has been achieved in a variety of commercial crops under normal field conditions, with no extraordinary use of sprays, irrigation, or fertilizer. These effects have been noted in various plants. Soybeans: with a +28.6% increase in yield by dry weight of Soybean seed (*Glycine max*) of variety 05–202, were exposed for 5 minutes to voltages of 5, 10, 20 and 30 kV on Mar. 2, 1994. One row of 48 seeds from each of these series was planted May 27, 1994 (25 days later) in individual field test plot. Emergence was noted as shown in FIG. 8A, with significant improvements over controls. The best emergence was seen in the 5 kV and 10 kV exposures. These two exposures were the same ones which showed increases in yield at harvest. The results are shown in Table 5.

TABLE 5

| Series | Voltage | Yield in Lbs. |
|---|---|---|
| Control | Controls | 1.75 lbs. |
| A | 5 kV | 2.25 lbs. |
| B | 10 kV | 2.20 lbs. |
| D | 20 kV | 1.63 lbs. |
| E | 30 kV | 1.50 lbs. |

Soybeans: In a 1995 field test, seeds of Soybean var. "Young" were treated Mar. 15, 1995 and planted May 12, 1995. Each field plot entry represents the mean of four replicates from a two pound lot of treated seed. Results were converted to bushels per acre. Weights per 1,000 seeds from harvest showed appreciable differences. Yield increases were the result of more soybeans produced. The results are shown in Table 6.

TABLE 6

| TREATMENT | BUSHELS/ACRE |
|---|---|
| Control | 35.95 |
| 4 kV, 10 sec. | 37.04 |
| 4 kV, 30 sec. | 34.99 |
| 4 kV, 5 min. | 36.04 |
| 8 kV, 10 sec. | 40.10 |
| 8 kV, 30 sec. | 41.44 |
| 8 kV, 5 min. | 41.73 |
| 12 kV, 10 sec. | 34.74 |
| 12 kV, 30 sec. | 39.50 |
| 12 kV, 5 min. | 39.64 |
| Control | 34.92 |

Field Corn: 24 seeds per lot were planted on May 31, 1995 in Blissfield, Mich. Figures are pounds of shelled corn per lot. The results are shown in Table 7.

TABLE 7

Inbred, Variety 305-10Gr (F6)

| VOLTAGE | 10 sec. | 30 sec. | 5 min. | Control |
|---|---|---|---|---|
| 4 kV | 2.65 lbs. | 1.85 | 1.55 | 2.10 |
| 8 kV | 1.80 | 1.95 | 1.45 | 1.95 |
| 12 kV | 1.95 | 1.35 | 1.50 | 1.90 |
| 16 kV | 1.60 | 1.00 | 0.95 | 2.00 |

Mean of Controls: 2.03

Hybrid, Variety HYPOP.2830MF. The results are shown in Table 8.

TABLE 8

| VOLTAGE | 10 sec. | 30 sec. | 5 min. | Control |
|---|---|---|---|---|
| 4 kV | 7.15 lbs | 7.10 | 6.65 | 5.55 |
| 8 kV | 5.05 | 4.40 | 4.75 | 4.90 |
| 12 kV | 5.95 | 5.65 | 4.85 | 4.20 |
| 16 kV | 5.20 | 5.95 | 5.10 | 6.10 |
| 20 kV | 5.20 | 4.75 | 3.95 | 3.20 |

Mean of Controls: 4.79

Carrots: Carrot seeds of variety *Daucus carota* Danvers 126 were planted May 31 1995 at Blissfield, Mich. and harvested Sep. 7, 1995. Weight per carrot figures are summarized by voltage in FIG. 10. Below are results per treatment duration for 4 kV and 8 kV (best yielding voltages) plus controls. In these results the interplay and dual importance of both time and voltage level is obvious. Here the increases over controls follow no linear progression, emphasizing the importance of the diagnostic procedures discussed earlier in order to select the most effective voltage and treatment duration for a particular seed variety. The results are shown in Table 9.

TABLE 9

| VOLTAGE | DURATION | WT./CARROT |
|---|---|---|
| 4 kV | 10 sec. | 0.10 lbs. |
| 4 kV | 30 sec. | 0.112 |
| 4 kV | 5 min. | 0.141 |
| 4 kV | 30 min. | 0.128 |
| 8 kV | 10 sec. | 0.066 lbs. |
| 8 kV | 30 sec | 0.154 |
| 8 kV | 5 min. | 0.175 |
| 8 kV | 30 min. | 0.093 |
| 0 | 0 | 0.10 lbs--Control |
| 0 | 0 | 0.096--Control |
| 0 | 0 | 0.105--Control |
| 0 | 0 | 0.089--Control |

0.098 - Mean of Controls

Tomatoes: Seeds of *Lycopersicon esculentum* variety malinta were exposed Mar. 10, 1995 and planted May 31, at Blissfield, Mich. and harvested Sep. 5, 1995. Yield in pounds of fruit per plant was averaged for each voltage across four time exposures (10 sec., 30 sec. 5 min., and 30 min). The results are shown in Table 10.

TABLE 10

| VOLTAGE | LBS./PLANT | % CHANGE |
|---|---|---|
| Control | 0.516 | 0% |
| 4 kV | 0.69 | +34% |
| 8 kV | 0.455 | -12% |
| 12 kV | 0.648 | +26% |
| 16 kV | 0.61 | +18% |
| 20 kV | 0.458 | -11% |

Rice: Cypress rice (*Oxyza sativa*) seed of variety Lemont was obtained from Mississippi State University, treated Mar. 12, 1995, and planted May 11, 1995 (59 days) in Mississippi. Test plots were flushed with water May 15 due to extreme dryness. Emergence occurred May 25 (delayed due to dryness) and plots were flooded June 9. Each figure is the result of 250 gms. of seed grown in four replicated plots, averaged and extrapolated to bushels per acre. Peak yield increases were noted as shown in Table 11.

TABLE 11

| VOLTAGE | TIME | YIELD | % CHANGE |
|---|---|---|---|
| Control | 0 | 159.37 | 0% |
| 16 kV | 10 sec. | 180.13 | +13% |
| 16 kV | 30 sec. | 169.06 | +6% |
| 8 kV | 5 min. | 170.08 | +7% |

FIGS. 11, 12 and 13 show the circuit 200 of the apparatus of the present invention. The apparatus is available from Hipotronics, Inc., Brewster, N.Y. There is an AC circuit 220 and a DC circuit 240. The negative terminal 260 is connected to the cathode electrode 12 and the positive terminal 280 is connected to the anode electrode 11. The various elements in the apparatus of FIG. 11 are shown in Table 12.

TABLE 12

| | |
|---|---|
| 220 Circuit | |
| C1 | .022 600 V |
| C2 | .022 600 V |
| PLI | |
| F2 | 2A |
| UP1 | |
| MDV1 | 250 V |
| 200 Circuit | |
| NE1 | |
| NE2 | |
| POS | Positive |
| NEG | Negative |
| R1 | 5 K ¼ W |
| R2 | 5 K 1% |
| R3 | 250 K 1% |
| R4 | 270 K |
| A2 | Meter Circuit P/N 30–293 |
| C1 | .22 400 V |
| C2 | .22 400 V |
| 201 Circuit | |
| T1 | Transformer |
| R1 | 250 M, 6 W |
| R2 | 250 M, 6 W |
| R3 | 50 K, 50 W |
| R4 | 50 K, 50 W |
| R5 | 200 M, 6 W |
| R6 | 22 M, 1 W |
| R7 | 22 M, 1 W |
| CR1 | Diode |
| CR2 | Diode |
| C1 | 0.02 µf; 30 kV |
| C2 | 0.02 µf; 30 kV |
| POS | Positive |
| NEG | Negative |
| Output | 60 kV DC |
| | 2.5 mADC |

FIGS. 15, 16 and 17 show the results of aging of the seeds for a period of time. As can be seen the aging is very important.

FIG. 18 shows the results when oat seeds are treated in the panicle which tends to shield the seed from the electrons. As can be seen, the treatment is effective but less so than in FIG. 17.

It is believed that the influence of the MIR process on seeds is based on the formation of electron-ion avalanches in air at normal atmospheric pressure and temperature. Under an applied electric potential, these avalanches can be directed as electron-ion impulses in the form of regular cycles or plasma waves. The frequency, amplitude and confinement of these pulses are governed by the applied potential and the design configurations of the MIR apparatus.

In the MIR process there is a relationship between the electron-ion avalanche pulse formation and the manner in which they form an organized plasma. The avalanche formation takes place between parallel plate electrodes 11 and 12 at a potential sufficient to cause the electrons ($e^-$) leaving the cathode to gain enough energy to ionize air molecules through both elastic, and to a lesser degree, inelastic collisions. In the present MIR configuration the minimum potential for avalanche formation is around 0.5 KV/cm. In the electron-molecule collisions new $e^-$'s are formed and these plus the primary $e^-$ keep repeating this process thus forming a cascading avalanche.

The mean number (n) of drifting electrons $e^-$'s grow at, $$n(x) = \exp(\alpha x) \quad (1)$$

wherein x is the distance of $e^-$ drift, and $\alpha$ the mean number of ionizing collisions per $e^-$ per cm. Nasser (E. Nasser, Fundamentals of Gaseous Ionization and Plasma Electronics, Wiley-Interscience, New York (1971)) points out that after a time t' the electric field disappears within the avalanche so that the $e^-$ swarm stops and attaches to molecules, that is, the plasma pulse is partially neutralized or discharged. This takes place inside the electrode gap if the drift path L of the avalanche is, $$L = vt' \quad (2)$$

wherein v, the $e^-$ drift velocity is less than the electrode spacing distance d (in air, v is around $10^7$ cm/sec.). With d=8 cm, t' must be $<8 \times 10^{-7}$ sec. The positive ions (not shown in FIG. 1A) have a low $v^+$ of around $10^5$ cm/sec and therefore have drifted very little from their point of production.

The current i produced by an avalanche is, $$i = (\epsilon n_0/t') \exp(\alpha v't) \quad (3)$$

If we take ($\epsilon n_0/t'$) as the rate constant k', for the avalanche formation, $$i = k' \exp(\alpha v'T) \quad (4)$$

where T is the transient time for one avalanche pulse, therefore $$\ln(i) = k(\alpha v'T) \quad (5)$$

wherein k is a new rate constant. Thus in (i) is proportional to the mean number of ionizing collisions ($\alpha$) during an avalanche pulse of transient time T.

One reliable criteria (H. Raether, Electron Avalanches and Breakdown in Gasses Butterworth & Co., Ltd., Great Britain (1964)) to know whether an observed current pulse can be identified with an avalanche process is to measure and compare the growth of $e^-$'s with the theoretical relationship.

$$n = \exp(\alpha v\, t) \quad (6)$$

In the MIR system there is no $e^-$ confinement, therefore the avalanche pulses drift laterally outside the confines of the parallel plate electrodes. This external drift of plasma provides a method for experimentally examining the growth of electrons as predicted by the Equation-6 theoretical relationship. For this purpose an experimental probe coil 101 consisting of 80,000 turns of #40 copper wire, was positioned in proximity with the MIR system (FIG. 5). When placed directly across one channel of a linear chart recorder, any induced magnetic field is readily detected as a voltage pulse in the probe coil 101. Avalanche pulses of varying current amplitudes were formed within the MIR system and recorded on a separate recorder channel as shown in FIG. 6. Any induced field in the probe coil is taken as being proportional to the plasma density formed by the ionizing collisions. From Equation 5 the predicted relationship between a transient avalanche current s and the magnetic field H, induced by an ion-electron concentration ($\alpha$) drifting across the test coil 101 would, under these hypothetical conditions be given by, $$H = c_1 ln(i) + c_2 \qquad (7)$$

wherein $c_1$ and $c_2$ are proportionality constants.

From chart recorder traces taken from experiments conducted over a range of electrode potentials, the amplitudes (in mv) of the plasma induced magnetic fields were compared with the amplitudes of the avalanche currents. These data (FIG. 7) plotted according to Equation 7 show good correlation ($r=0.89$; $P<0.05$) between the theoretical model of plasma avalanches and the experimental data obtained from the MIR system.

At a given potential the amplitudes and frequency of the avalanche pulses remain relatively constant over the transient intervals. The stability of the ion current pulses was examined by "injecting" excess electrons into an MIR system during a succession of stable avalanche pulses. If UV radiation is directed onto the cathode plate, electrons are released through the photoelectric effect. This can produce what has been called (H. Raether, Electron Avalanches and Breakdown in Gasses, Butterworth & Co., Ltd., Great Britain (1964)) "Avalanches With Successors". Through the injection of additional secondary electrons the amplitudes of the avalanche pulse currents are increased.

This photoelectric avalanche enhancement was produced in a MIR. system consisting of "Optical Transmitting Electrodes" or OTE's (glass coated with a semiconducting tin oxide film) as electrode 12 arranged with electrode separation of 6 cm and 20 kV applied potential. As shown in FIG. 14, the effect of the electron injection is shown to take place 30 seconds after the start (indicated by arrow) of cathode exposure. Due to a shielding effect (E. Nasser, Fundamentals of Gaseous Ionization and Plasma Electronics, Wiley-Interscience, New York (1971)), a plasma will tend to remain stable even when external charges are introduced into the avalanche system. This initial delay followed by a rise to a maximum current amplitude at around 70 sec. followed by the gradual decline, is very consistent with the results obtained in other plasma systems, again confirming that it is a plasma electron avalanche process at work in the space between the electrodes. Exposure of the anode (polarity reversed) to UV had no effect (lower curve) on the current pulse amplitudes, as would be expected. using an anode which is wider than the cathode alters the shape of the electric field in a manner which contains more of the ion/electrons between the electrodes, allowing fewer to drift outside. The result is even more uniform and regular pulses of ion/electron avalanches.

The commercial advantages of the present invention are:

(1) Germination and Early Growth: With the MIR method the plant moves through the vulnerable, seedling stage faster. Greater uniformity at this stage limits the disadvantages of taller plants shading shorter ones and increases chances for all to thrive. Uniformity of growth also makes it easier to harvest the plants.

(2) Root Growth: The MIR method is of particular value in plants such as navy beans where root growth is frequently a problem.

(3) Accelerated Maturity: Accelerated maturity due to the MIR method is of economic advantage to farmers in crops, such as tomato and sweet corn, where the first produce to market each season commands much higher prices. In countries which double crop, it increases the likelihood that both crops will be able to mature and produce a full harvest. In far northern regions, with limited daylight and warm days in growing season, the MIR method increases the chances of a successful season.

(4) Increased Yield: There are economic and humanitarian advantages to the MIR method. There is commercial appeal to the farmer, allowing him to grow more crop to produce income from the same farm. With world population growth outstripping food supply, any significant increases in yield is beneficial.

Key features of the MIR method are:

(1) Sharp, well-organized, uniform electron avalanches (not corona discharge, and not static electric fields). This is provided with a DC voltage source having an AC ripple.

(2) Voltage potentials are 0.2 vK/cm to (but not including) dielectric spark gap breakdown discharge.

(3) Anode electrode with the seeds.

(4) Special electron feedback loop 15 enhances results.

(5) Diagnostic Procedures.

(6) A waiting period of several weeks between treatment and planting.

(7) Redox ratio measurement provides quality control after treatment by the MIR method to confirm if effect was achieved, thus providing an immediate check on results.

(8) Coil 101 recorder system provides an additional quality control to insure avalanches are in fact being produced, and have the proper form. Without this test, humidity and dust/debris on electrodes 11 and/or 12 could cause failure to produce avalanches (particularly when operating near the 0.5 kV/cm threshold, which is frequently used with some seeds.

(9) The MIR method is practical and affordable for large scale commercial operations. Short time period of treatments are required (seconds to minutes) and small amounts of electricity are expended. The MIR method is suitable for conveyor-driven seed handling systems. The MIR method produces consistency of results.

It is intended that the foregoing description be only illustrative of the present invention and that the present invention be limited only by the hereinafter appended claims.

We claim:

1. An apparatus for treating a seed to enhance the growth characteristics of the seed which comprises:

(a) a pair of spaced apart electrodes as an anode and as a cathode having a gap between them wherein the seed is to be supported on or adjacent to the anode;

(b) voltage generating means for simultaneously supplying a direct current (DC) voltage to the anode and the cathode using a power supply with an output voltage with an impressed alternating current AC ripple as the output voltage so as to produce organized, pulsed avalanches of electrons moving from the cathode towards and into a seed when placed on the anode for a period of time which enhances the growth characteristics of the seed; and (c) coil means with multiple turns mounted adjacent to the spaced apart electrodes which detects pulsed avalanches of electrons; and (d) recording means for recording the pulsed avalanches of electrons as detected by the coil means.

2. The apparatus of claim 1 wherein the DC voltage to be supplied is between about 4K and a spark breakdown voltage, the AC voltage to be supplied is between about 60 and 220 Hz and the gap is between about 1 and 20 cm.

3. The apparatus of claim 1 wherein the detection means is a coil which has between about 10,000 and 100,000 turns.

4. The apparatus of claim 1 wherein the recording means is a chart recorder.

5. The apparatus of claim 1 wherein air is provided in the gap.

6. The apparatus of claim 1 wherein the anode and cathode have legs made of a dielectric material which rest upon a non-conductive table and wherein a feedback conductor leads back to anode from the table.

* * * * *